(12) United States Patent
Martin et al.

(10) Patent No.: US 9,883,858 B1
(45) Date of Patent: Feb. 6, 2018

(54) SUTURING INSTRUMENT WITH ROBOTIC DRIVE INTERFACE

(71) Applicant: Ethicon Endo-Surgery, LLC, Guaynabo, PR (US)

(72) Inventors: David T. Martin, Milford, OH (US); Christopher J. Hess, Cincinnati, OH (US); William J. White, West Chester, OH (US); Daniel J. Mumaw, Liberty Township, OH (US); Andrew C. Deck, Dayton, OH (US); Daniel L. Geiger, Ft. Thomas, KY (US); Frederick E. Shelton, IV, Hillsboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 396 days.

(21) Appl. No.: 14/739,415

(22) Filed: Jun. 15, 2015

(51) Int. Cl.
| | |
|---|---|
| *A61B 17/04* | (2006.01) |
| *A61B 17/29* | (2006.01) |
| *A61B 17/06* | (2006.01) |
| *A61B 19/00* | (2006.01) |
| *A61B 17/062* | (2006.01) |
| *A61B 17/00* | (2006.01) |

(52) U.S. Cl.
CPC ........ *A61B 17/0469* (2013.01); *A61B 17/062* (2013.01); *A61B 17/06066* (2013.01); *A61B 17/29* (2013.01); *A61B 19/56* (2013.01); *A61B 19/2203* (2013.01); *A61B 2017/00407* (2013.01); *A61B 2017/2926* (2013.01)

(58) Field of Classification Search
CPC .......... A61B 17/0469; A61B 17/06133; A61B 17/062; A61B 17/0625; A61B 2017/00473; A61B 2017/0608; A61B 2017/0023; A61B 2017/0479; A61B 2090/0811; A61B 2017/00477
See application file for complete search history.

(56) References Cited

U.S. PATENT DOCUMENTS

| | | | |
|---|---|---|---|
| 5,792,135 A | 8/1998 | Madhani et al. | |
| 5,817,084 A | 10/1998 | Jensen | |
| 7,524,320 B2 * | 4/2009 | Tierney | G06Q 30/02 606/1 |
| 7,766,925 B2 * | 8/2010 | Stokes | A61B 1/00087 606/139 |
| 7,935,128 B2 * | 5/2011 | Rioux | A61B 17/0469 606/144 |

(Continued)

*Primary Examiner* — Eric Rosen
*Assistant Examiner* — Son Dang
(74) *Attorney, Agent, or Firm* — Frost Brown Todd LLC

(57) ABSTRACT

A surgical instrument includes cartridge receiving assembly, a shaft assembly, and an interface assembly. The cartridge receiving assembly is operable to receive a needle driving cartridge. The shaft assembly includes a first actuation member that is operable to actuate the cartridge receiving assembly to thereby drive a needle from a needle driving cartridge received in the cartridge receiving assembly. The interface assembly includes a base and a plurality of drive shafts extending upwardly from the base. The drive shafts extend along respective axes that are perpendicular to the longitudinal axis of the shaft assembly. The drive shafts are rotatable independently relative to each other. A first drive shaft of the plurality of drive shafts is operable to drive the first actuation member. The interface assembly is configured to couple with a robotic control system.

17 Claims, 21 Drawing Sheets

(56) References Cited

U.S. PATENT DOCUMENTS

| | | | |
|---|---|---|---|
| 7,993,354 B1 * | 8/2011 | Brecher | A61B 17/0482 606/145 |
| 8,057,386 B2 * | 11/2011 | Aznoian | A61B 1/00087 600/104 |
| 8,118,820 B2 * | 2/2012 | Stokes | A61B 17/0469 606/139 |
| 8,187,288 B2 * | 5/2012 | Chu | A61B 17/0469 606/144 |
| 8,236,013 B2 * | 8/2012 | Chu | A61B 17/0401 606/139 |
| 8,616,431 B2 | 12/2013 | Timm et al. | |
| 8,702,732 B2 | 4/2014 | Woodard, Jr. et al. | |
| 8,821,518 B2 * | 9/2014 | Saliman | A61B 17/0469 606/144 |
| 9,072,535 B2 | 7/2015 | Shelton et al. | |
| 9,125,645 B1 * | 9/2015 | Martin | A61B 17/0469 |
| 9,168,037 B2 | 10/2015 | Woodard, Jr. et al. | |
| 9,357,998 B2 * | 6/2016 | Martin | A61B 17/0483 |
| 9,375,212 B2 | 6/2016 | Martin et al. | |
| 9,474,522 B2 | 10/2016 | Deck et al. | |
| 2006/0069396 A1 * | 3/2006 | Meade | A61B 17/0482 606/144 |
| 2009/0312772 A1 * | 12/2009 | Chu | A61B 17/0469 606/144 |
| 2010/0152751 A1 * | 6/2010 | Meade | A61B 17/0469 606/144 |
| 2012/0232567 A1 * | 9/2012 | Fairneny | A61B 17/0469 606/147 |

\* cited by examiner

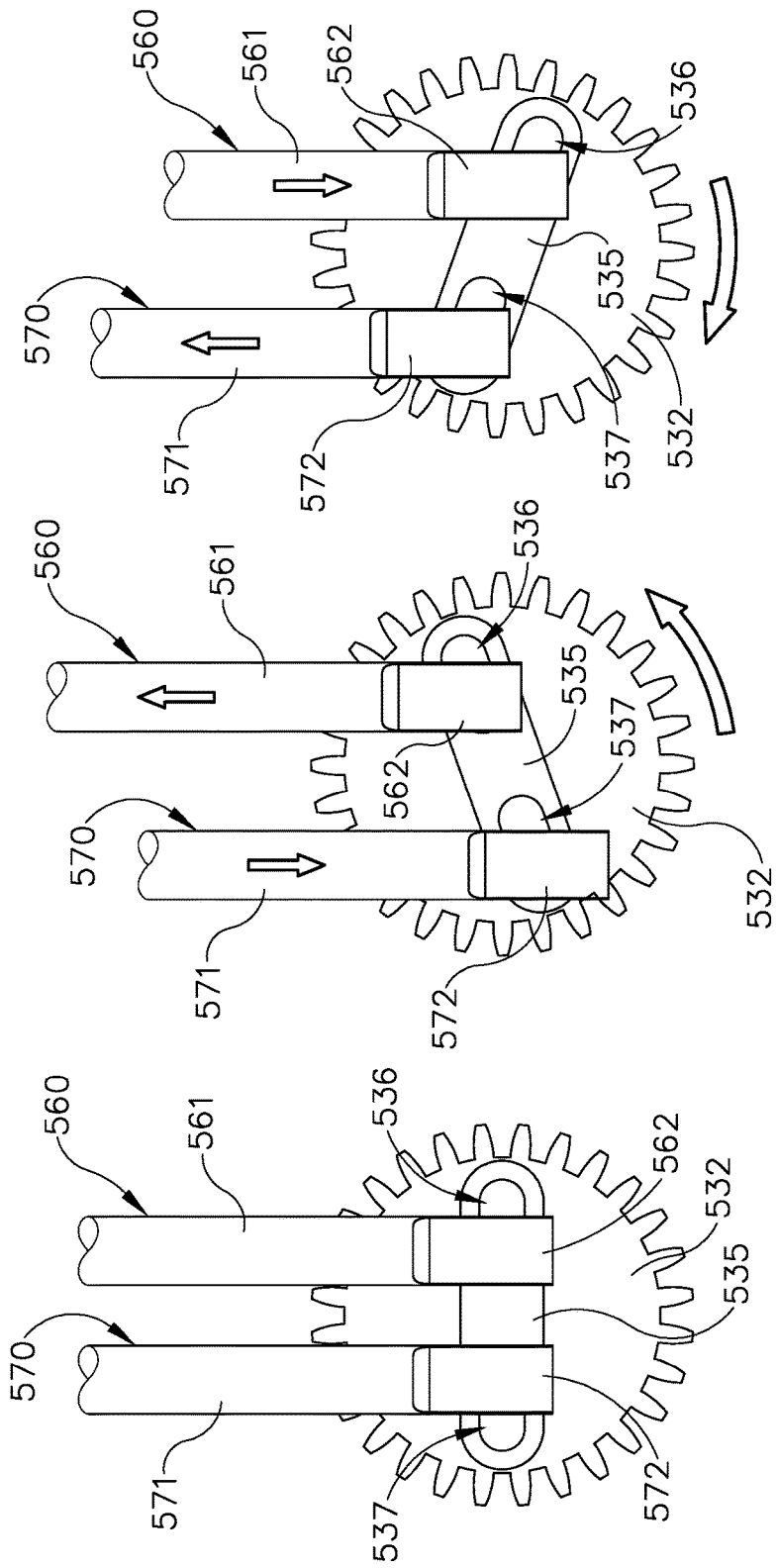

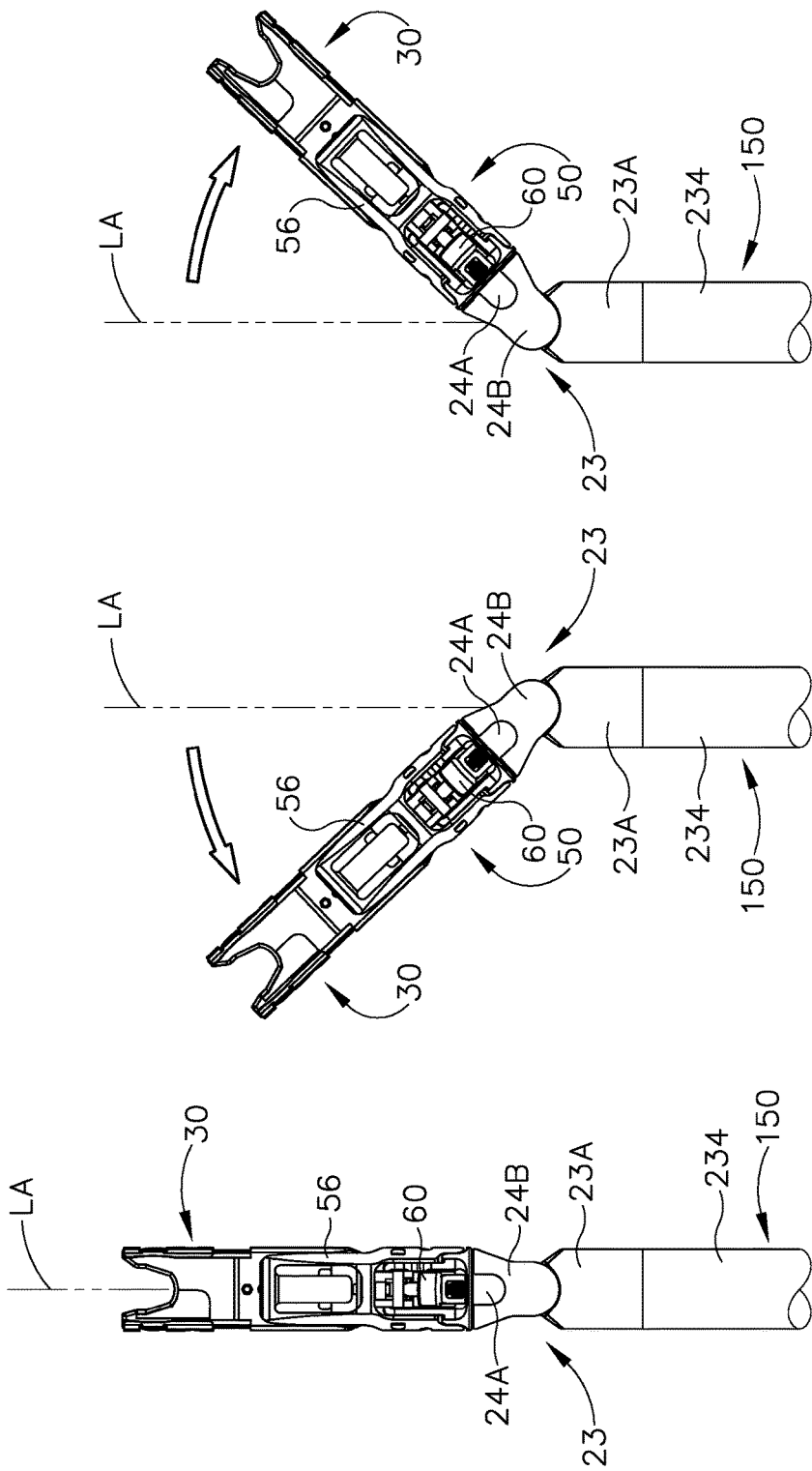

SUTURING INSTRUMENT WITH ROBOTIC DRIVE INTERFACE

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laproscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, now U.S. Pat. No. 9,168,037, issued Oct. 27, 2015, the disclosure of which is incorporated by reference herein; U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; and U.S. patent application Ser. No. 14/297,993, entitled "Jawed Cartridge receiving assembly for Needle Cartridge," filed Jun. 6, 2014, now U.S. Pat. No. 9,474,522, issued Oct. 25, 2016, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, suturing instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; and U.S. Pub. No. 2012/0298719, entitled "Surgical Stapling Instruments with Rotatable Staple Deployment Arrangements," published Nov. 29, 2012, now U.S. Pat. No. 9,072,535, issued Jul. 7, 2015, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 22A depicts the gear member and articulation drive rods of the articulation drive components of FIG. 19 in a first configuration;

FIG. 22B depicts the gear member and articulation drive rods of the articulation drive components of FIG. 19 in a second configuration;

FIG. 22C depicts the gear member and articulation drive rods of the articulation drive components of FIG. 19 in a third configuration;

FIG. 23A depicts a top plan view of the cartridge receiving assembly of FIG. 2A, the cartridge of FIG. 3A, and the shaft assembly of the drive interface assembly of FIG. 7, with the cartridge receiving assembly aligned with the longitudinal axis of the shaft assembly;

FIG. 23B depicts a top plan view of the cartridge receiving assembly of FIG. 2A, the cartridge of FIG. 3A, and the shaft assembly of the drive interface assembly of FIG. 7, with the cartridge receiving assembly deflected in a first direction away from the longitudinal axis of the shaft assembly by the articulation drive components of FIG. 19; and FIG. 23C depicts a top plan view of the cartridge receiving assembly of FIG. 2A, the cartridge of FIG. 3A, and the shaft assembly of the drive interface assembly of FIG. 7, with the cartridge receiving assembly deflected in a second direction away from the longitudinal axis of the shaft assembly by the articulation drive components of FIG. 19.

Figure 1:
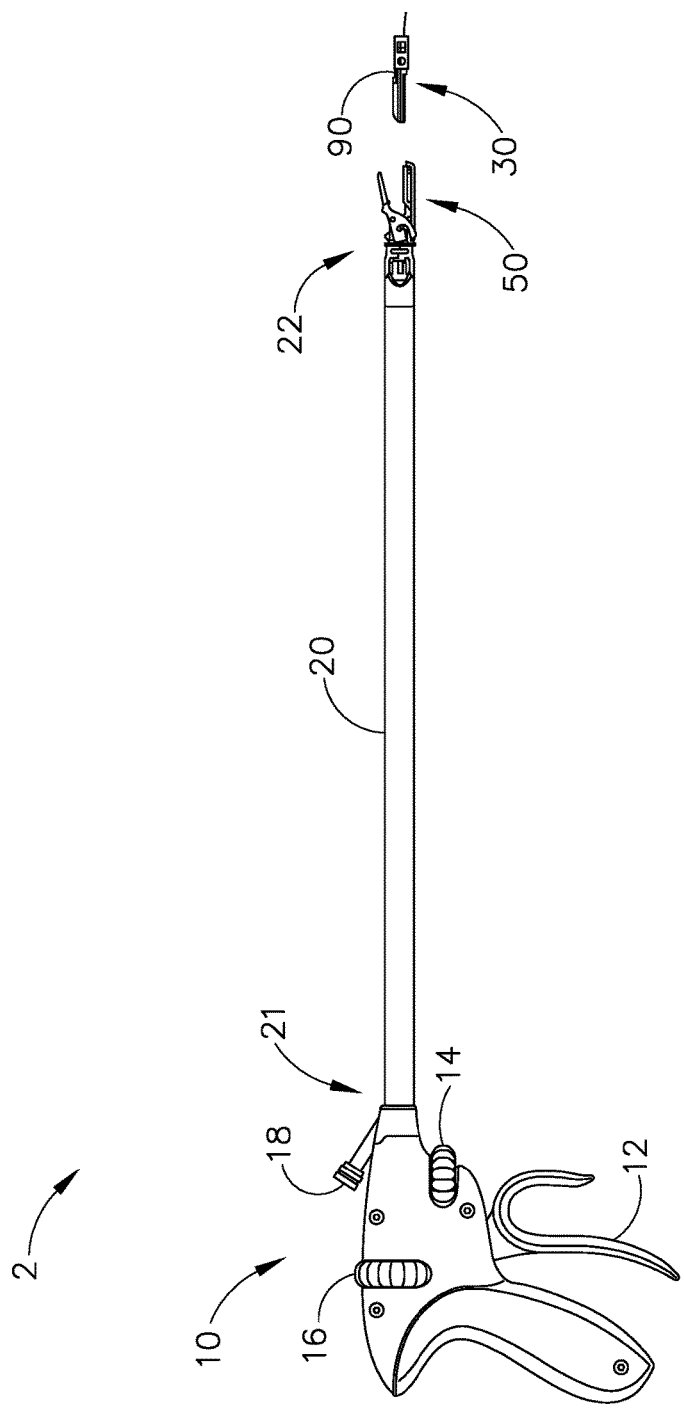
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Surgical Suturing Instrument

FIG. 1 illustrates an example of a surgical suturing instrument (2). Instrument (2) comprises a handle assembly (10), an elongate shaft (20), and a cartridge receiving assembly (50), which is operable to receive a needle applier cartridge (30). Shaft (20) has a proximal end (21), a distal end (22), and a longitudinal axis extending therebetween. Handle assembly (10) is connected to the proximal end (21) of the shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to the distal end (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first input (12), shown here as a trigger that pivots between opened and closed positions, may be used to selectively actuate needle applier cartridge (30). The trigger may be spring biased to return the trigger to its open position. A second input (14), shown here as a rotary knob, may be used to selectively articulate shaft (20). A third input (16), shown here as a rotary knob, may be used to selectively rotate needle applier cartridge (30) about shaft (20). Of course, the number, type, configuration, and operation of inputs (12, 14, 16) may vary.

Figure 2A:
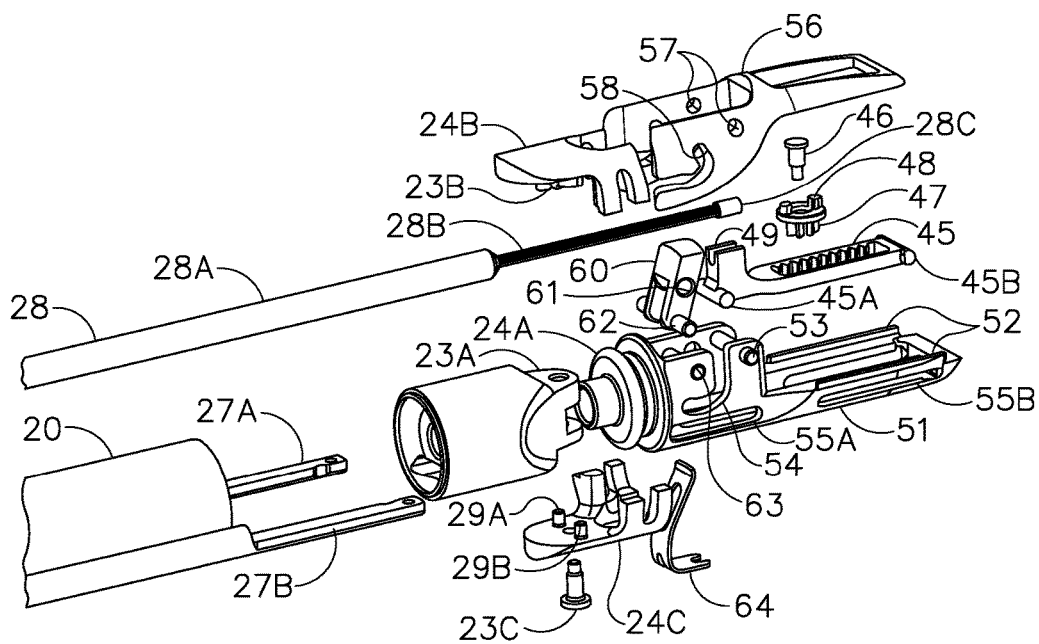
FIG. 2A depicts top perspective exploded view of a cartridge receiving assembly of the instrument of FIG. 1.
Figure 2B:
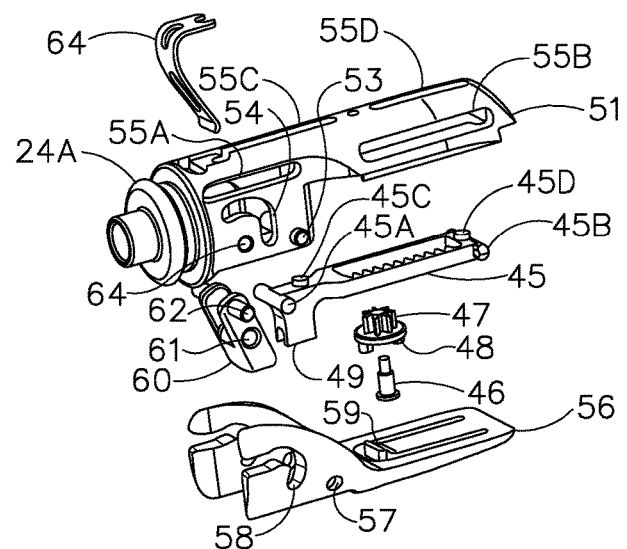
FIG. 2B depicts bottom perspective exploded view of the cartridge receiving assembly of FIG. 2A.

FIGS. 2A-2B illustrate exploded views of cartridge receiving assembly (50) of the present example. Distal end (22) of shaft (20) comprises an articulation joint (23) and a rotational bearing (24). Articulation joint (23) includes a knuckle (23A) that receives pins (23B, 23C), which are connected to bearing supports (24B, 24C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to second input (14) to opposingly push and pull rods (27A, 27B). In other words, second input (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by the pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first input (12) and to third input (16). Actuation of first input (12) will impart axial push and pull loads on drive rod (28) to longitudinally reciprocate rack (45) and thereby actuate needle applier cartridge (30). Actuation of third input (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the open configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
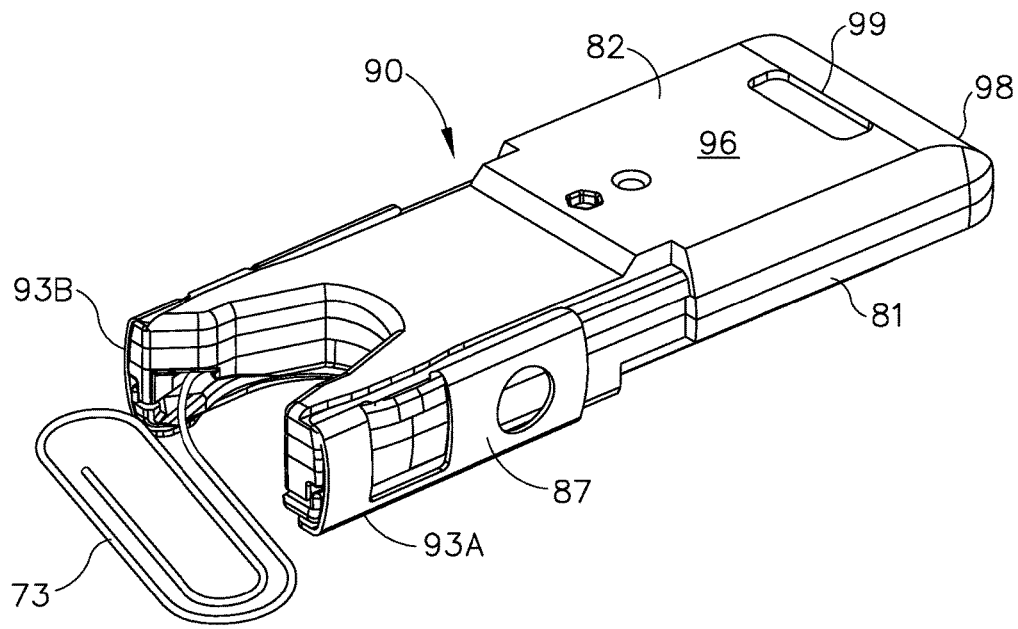
FIG. 3A depicts a top perspective view of an exemplary cartridge configured for receipt in the cartridge receiving assembly of FIG. 2A.
Figure 3B:
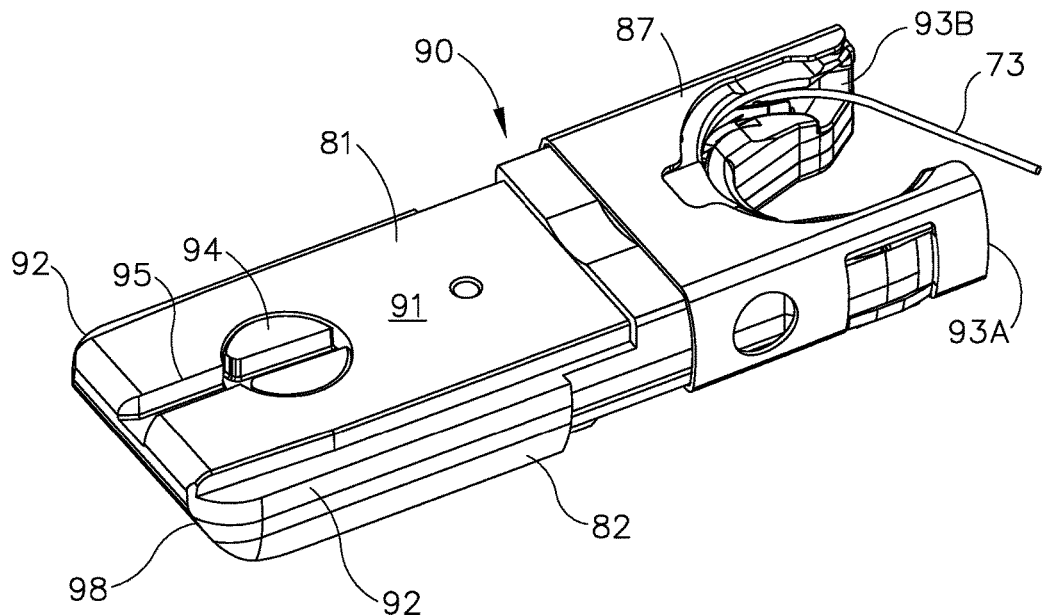
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
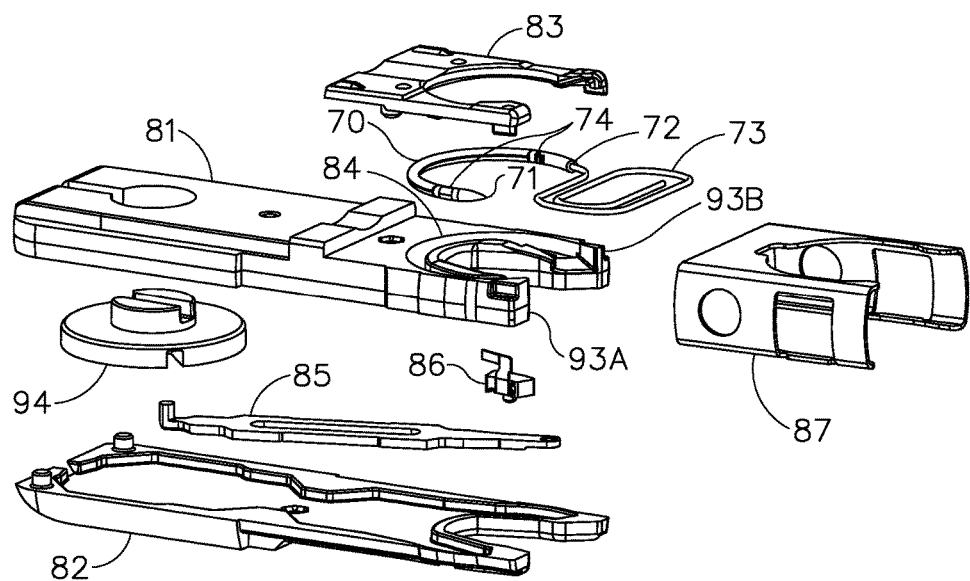
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from the trailing end (72). Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
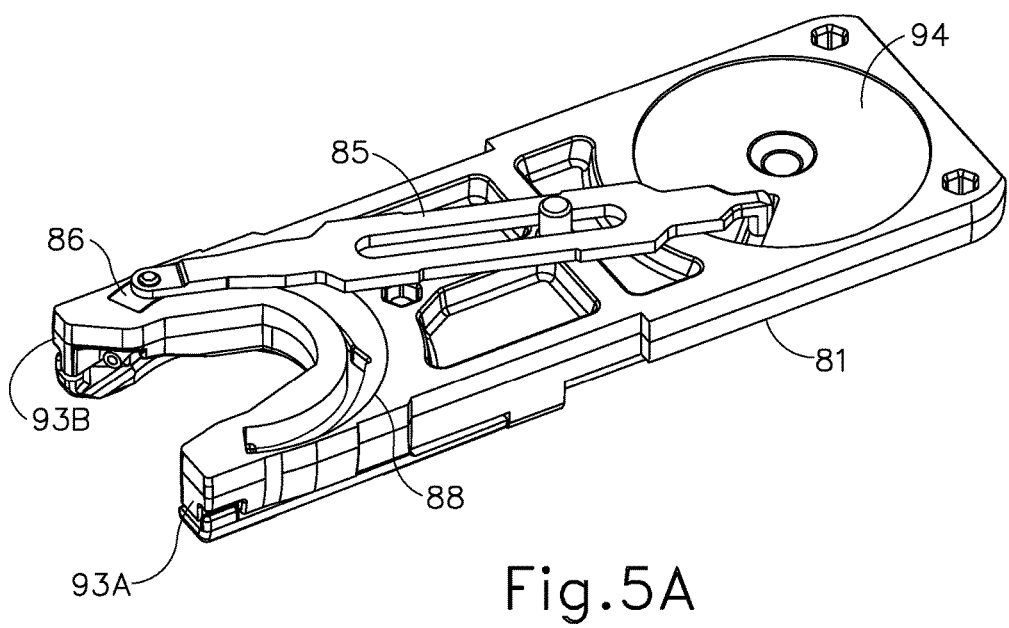
FIG. 5A depicts a perspective view of a drive assembly of the cartridge of FIG. 3A, with the drive assembly at one end of its stroke.
Figure 5B:
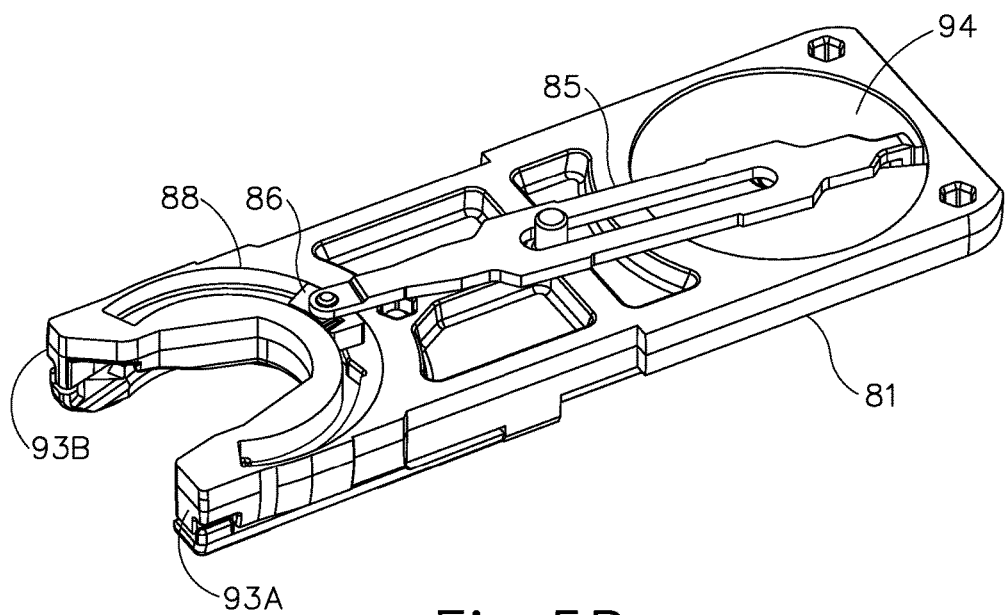
FIG. 5B depicts a perspective view of the drive assembly of FIG. 5A, with the drive assembly at mid-stroke.
Figure 5C:
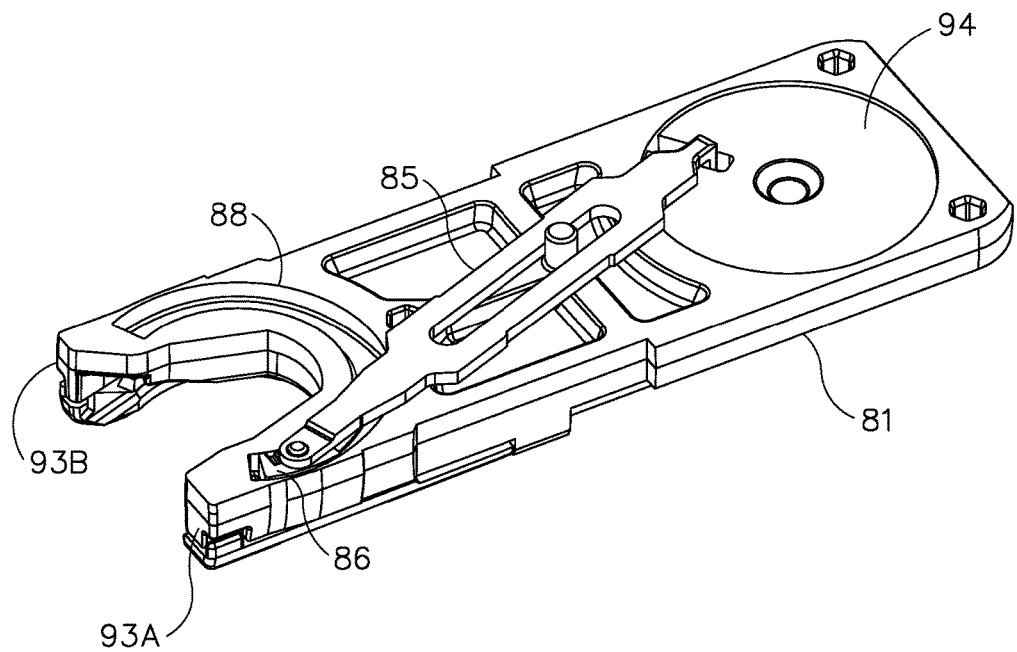
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) omitted from FIGS. 5B-5C. Needle driver (86) rides in a carrier track (88) and extends into needle track (84) to engage and drive needle (70). A link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
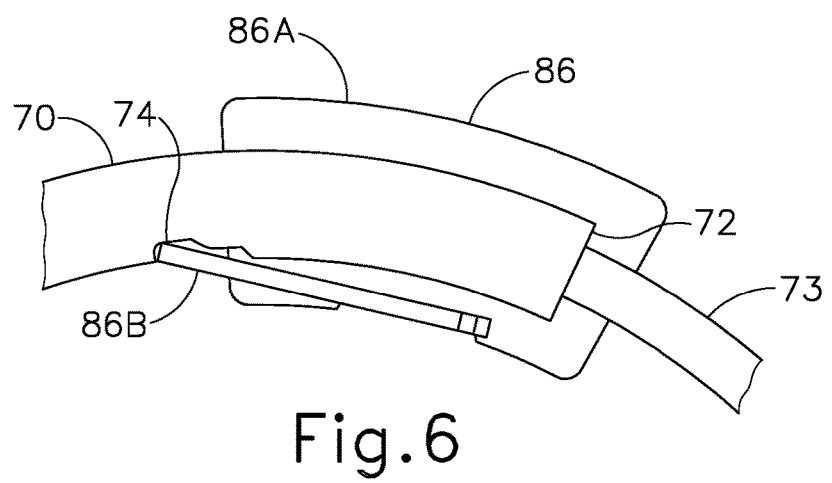
FIG. 6 depicts a partial plan view of a needle driver of the cartridge of FIG. 3A engaging a needle of the cartridge of FIG. 3A.

FIG. 6 illustrates a detailed view of needle driver (86) engaging needle (70).

Needle driver (86) comprises a carrier (86A) and a driver (86B). Carrier (86A) is dimensioned to slideably fit in carrier track (88). Driver (86B) is attached to carrier (75) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C, when first input (12) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (95) and entrance port (97). Tissue interposed between arms (93A, 93B) will be pierced by leading end (71) of needle (70).

When first input (12) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first input (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) will follow needle (70) and be threaded through the pierced tissue.

When first input (12) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first input (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, now U.S. Pat. No. 9,474,522, issued Oct. 25, 2016, the disclosure of which is incorporated by reference herein; and U.S. patent application Ser. No. 14/298,038, entitled "Circular Needle Applier with Cleats," filed Jan. 30, 2015, now U.S. Pat. No. 9,375,212, issued Jun. 28, 2016, the disclosure of which is incorporated by reference herein. It should be understood that such details, explanations, examples, and alternative embodiments may be readily applied to the above-described instrument (10) and subcomponents thereof.

II. Exemplary Robotic Drive Assembly Interface for Suturing Instrument

A. Overview

In some instances, it may be beneficial to modify surgical suturing instrument (2) described above with elements that will enable instrument to be controlled robotically. For example, it may be beneficial to modify or replace handle assembly (10) with an interface that is configured to couple with a robotic control system. Thus, instead of utilizing inputs (12, 14, 16), which may be more suitable for handheld control of surgical suturing instrument (2), alternate input controls may be utilized for robotic control. The following description relates to an assembly that is configured to interface with a robotic control system like a system as described in U.S. Pat. No. 5,792,135; U.S. Pat. No. 5,817, 084; U.S. Pat. No. 7,524,320; U.S. Pub. No. 2012/0132450, now U.S. Pat. No. 8,616,431; and/or U.S. Pub. No. 2012/0298719, now U.S. Pat. No. 9,072,535, the disclosures of which are incorporated by reference herein. However, it should be understood that the following teachings may be readily modified to enable the assembly to interface with other kinds of robotic control systems.

FIGS. 7-10 show multiple views of an assembled robotic drive assembly interface (100) for a suturing instrument like instrument (2) described above. It should be understood that instrument (2) may readily incorporate drive assembly interface (100) in place of handle assembly (10). Drive assembly interface (100) comprises a base (116) defining a plurality of apertures (110), a mounting plate (114) configured to mount to a robotic arm (not shown), a shaft support structure (122), four drive discs (120a, 120b, 120c, 120d), a sheath rotation drive (200), a cartridge receiving assembly rotation drive (300), a needle drive (400), and an articulation drive (500).

A shaft assembly (150) extends distally from drive assembly interface (100). Shaft assembly (150) comprises an outer sheath (234) and other movable drive components as will be described in greater detail below. Shaft support structure (122) extends upwardly from base (116) and provides support to outer sheath (234) (while still allowing outer sheath (234) to rotate). By way of example only, shaft support structure (122) may include a bushing, bearings, and/or other features that facilitate rotation of outer sheath (234) relative to support structure (122).

Figure 7:
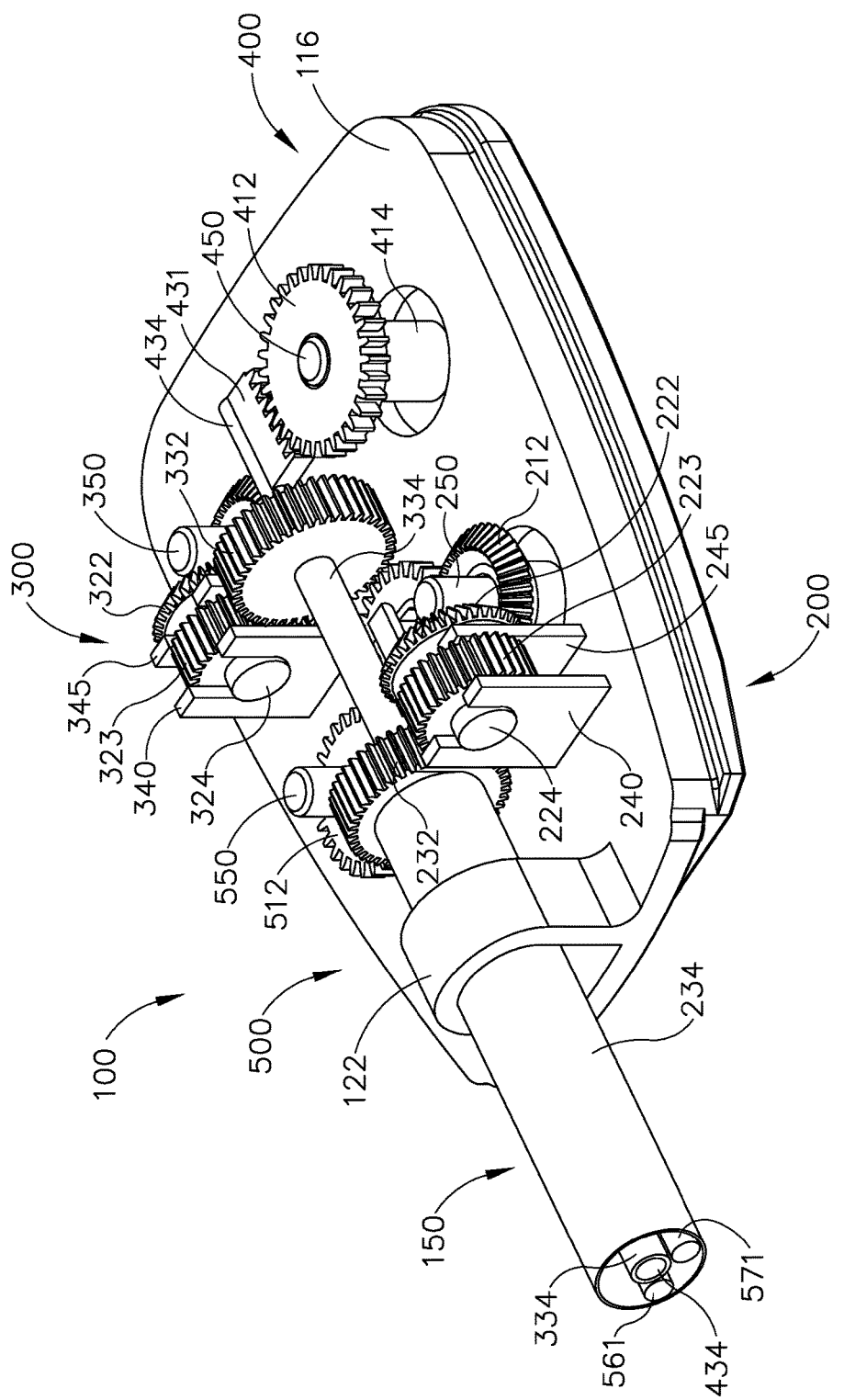
FIG. 7 depicts a perspective view of an exemplary robotic system drive interface assembly that may be incorporated into the instrument of FIG. 1 in place of the handle assembly.
Figure 8:
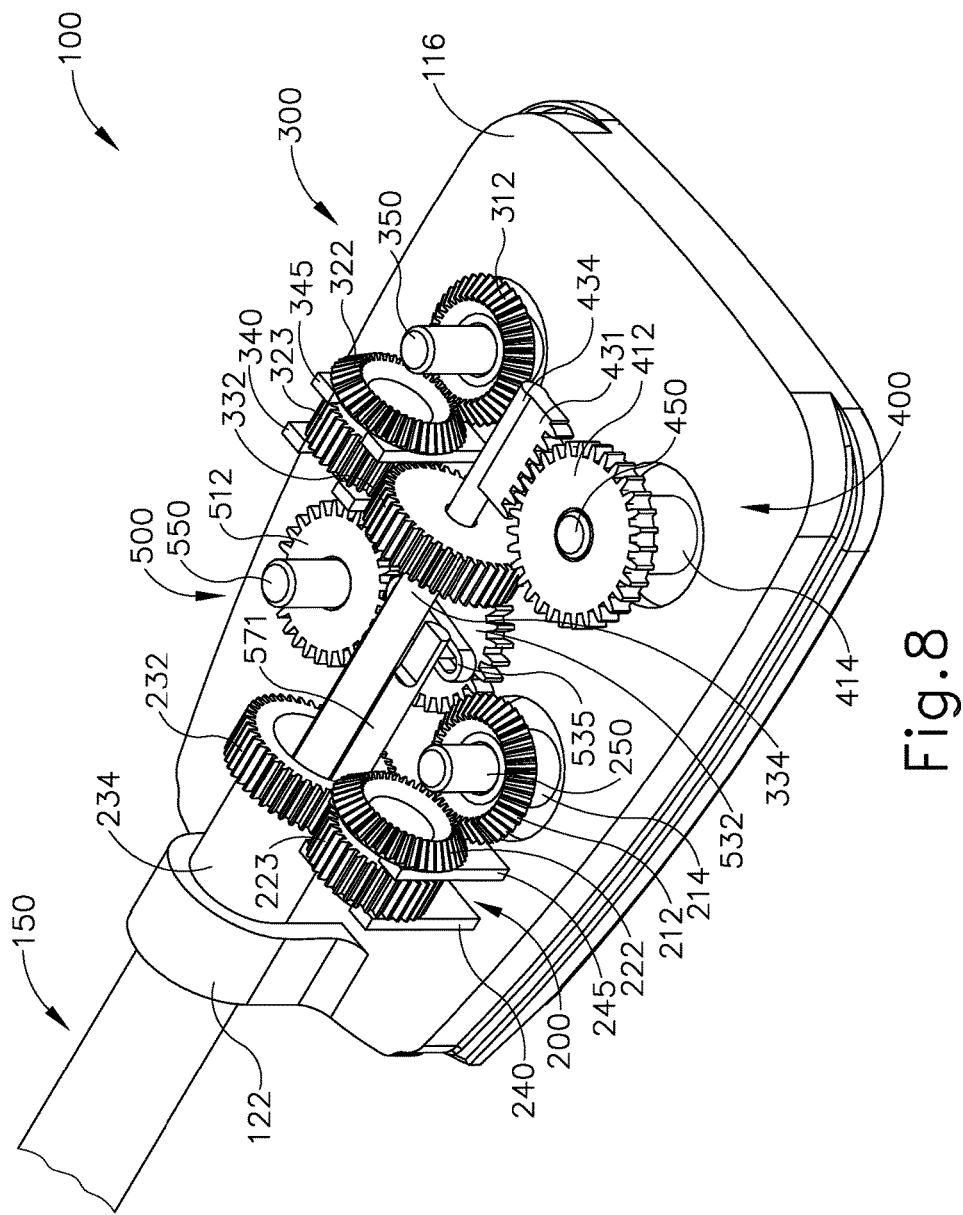
FIG. 8 depicts another perspective view of the drive interface assembly of FIG. 7.
Figure 9:
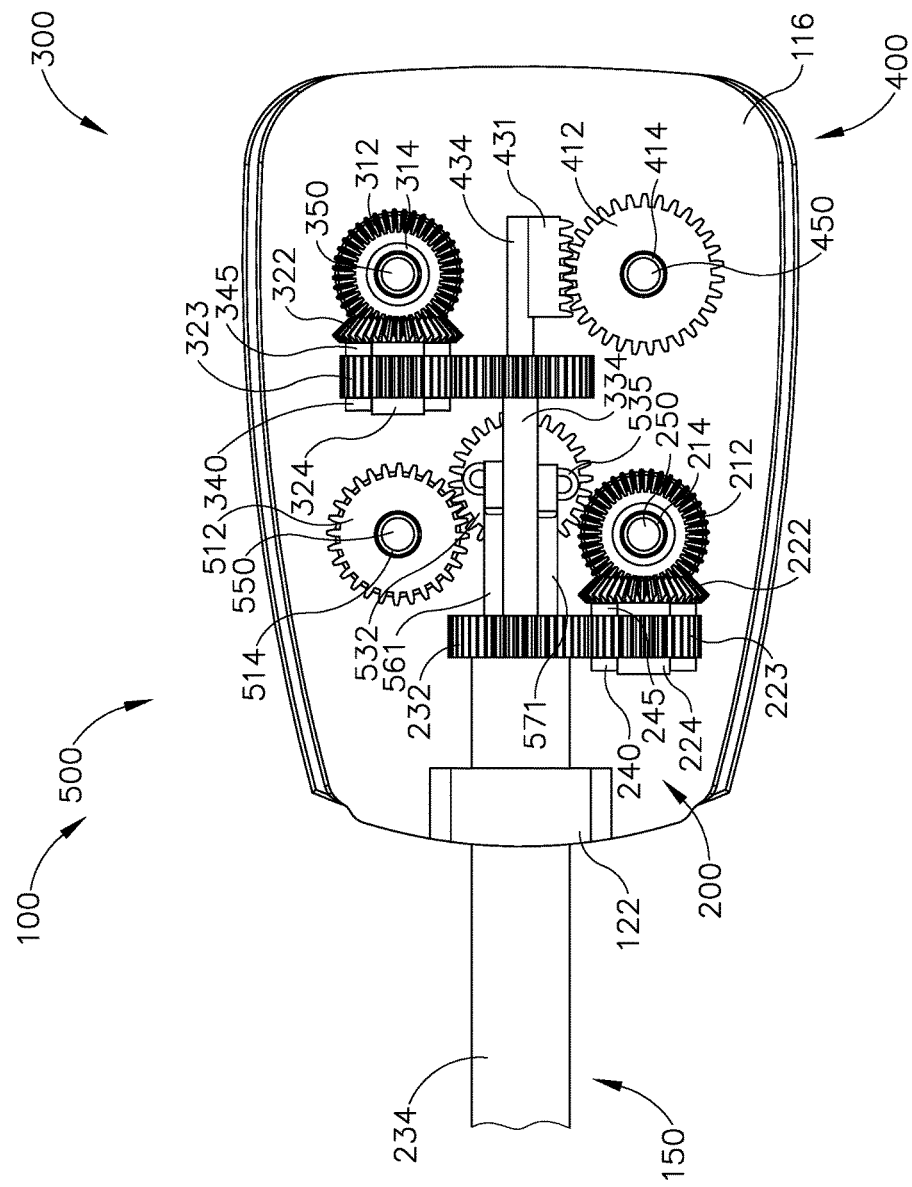
FIG. 9 depicts a top plan view of the drive interface assembly of FIG. 7.
Figure 10:
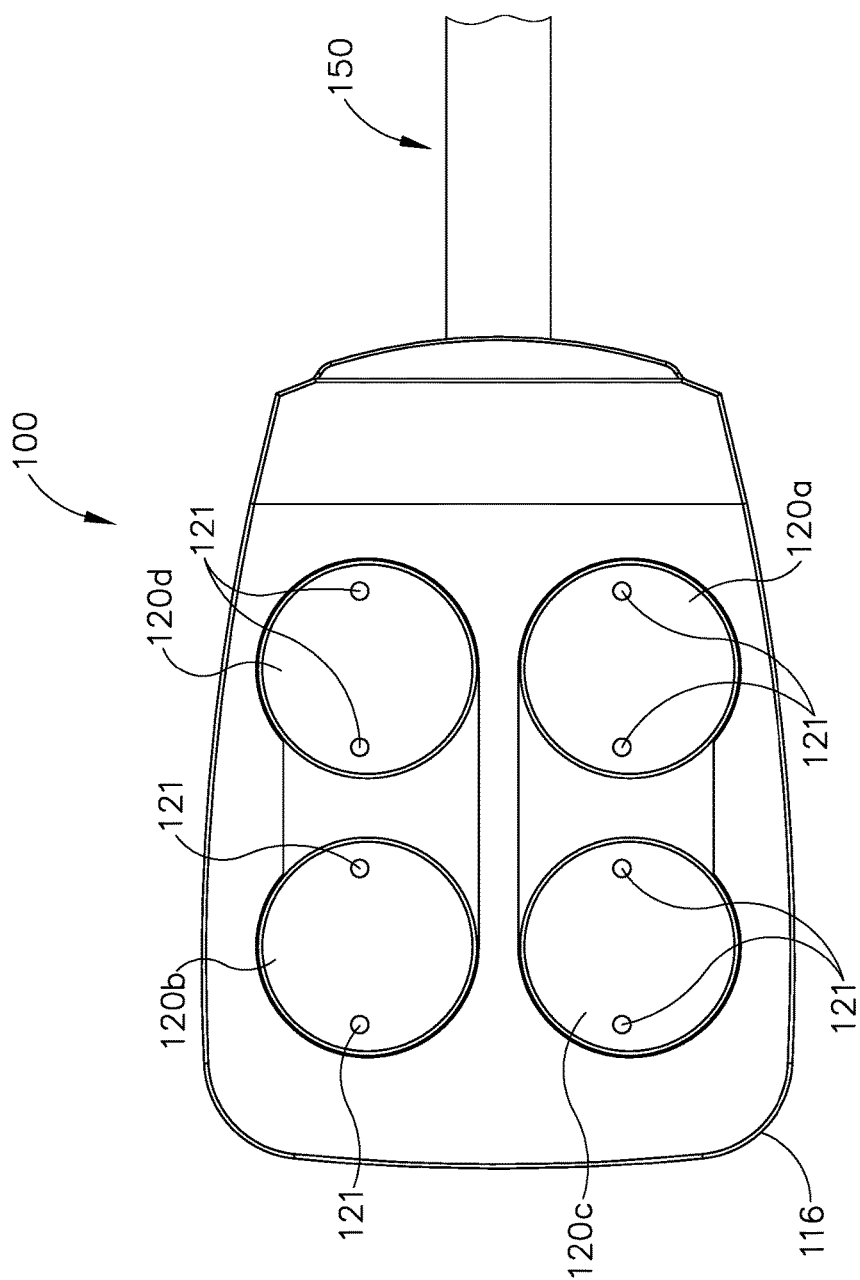
FIG. 10 depicts a bottom plan view of the drive interface assembly of FIG. 7.

As shown in FIG. 10, base (114) further includes four drive discs (120a, 120b, 120c, 120d) that are rotatable relative to plate (116). Each disc (120) includes a pair of unitary pins (121) that couple with complementary recesses (not shown) in drive elements of robotic arm (not shown). In some versions, one pin (121) of each pair is closer to the axis of rotation of the corresponding disc (120a, 120b, 120c, 120d), to ensure proper angular orientation of disc (120a, 120b, 120c, 120d) relative to the corresponding drive element of robotic arm (not shown). As best seen in FIGS. 7-8, a drive shaft (250, 350, 450, 550) extends unitarily upwardly from each disc (120a, 120b, 120c, 120d). As will be described in greater detail below, discs (120a, 120b, 120c, 120d) are operable to provide independent rotation of sheath rotation drive (200), cartridge receiving assembly rotation drive (300), need drive (400), and articulation drive, through independent rotation of drive shafts (250, 350, 450, 550).

B. Exemplary Shaft Assembly Rotation Drive Components

Figure 11:
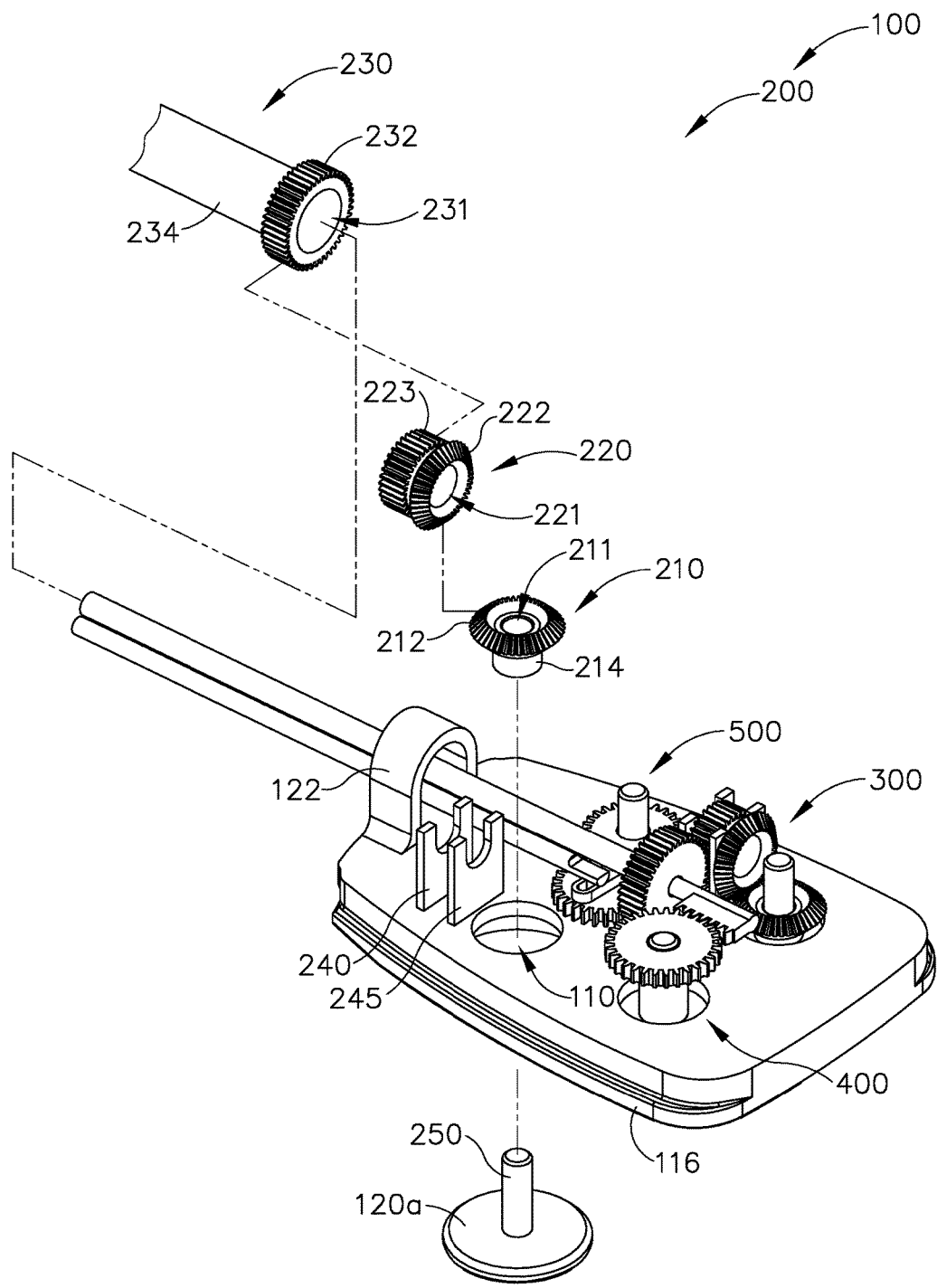
FIG. 11 depicts a perspective view of the drive interface assembly of FIG. 7, with shaft rotation drive components shown exploded from the rest of the drive interface assembly.
Figure 13:
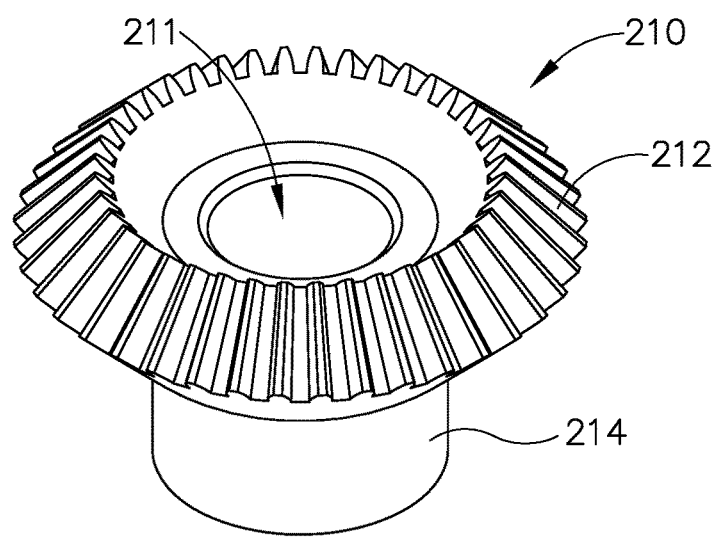
FIG. 13 depicts a perspective view of a second drive gear member of the shaft rotation drive components of FIG. 11.

As shown in FIG. 11, sheath rotation drive (200) includes drive disc (120a), drive shaft (250), a first rotary member (210), an idler member (220), and a second rotary member (230). As best seen in FIG. 13, first rotary member (210) comprises a first bevel gear (212) unitarily fixed to a coupling shaft (214). Referring back to FIG. 11, coupling shaft (214) extends through aperture (110). First bevel gear (212) and coupling shaft (214) together define a bore (211). However, it should be noted that coupling shaft (214) alone may define bore (211). Bore (211) is dimensioned to receive drive shaft (250) through an interference fit so that first rotary member (210) and drive shaft (250) are unitarily fixed together. Of course, any other means of fixing drive shaft (250) to first rotary member (210) may be used, such as welding. It should be understood that rotation of drive disc (120a) also provides rotation to drive shaft (250) and first bevel gear (212).

Figure 12:
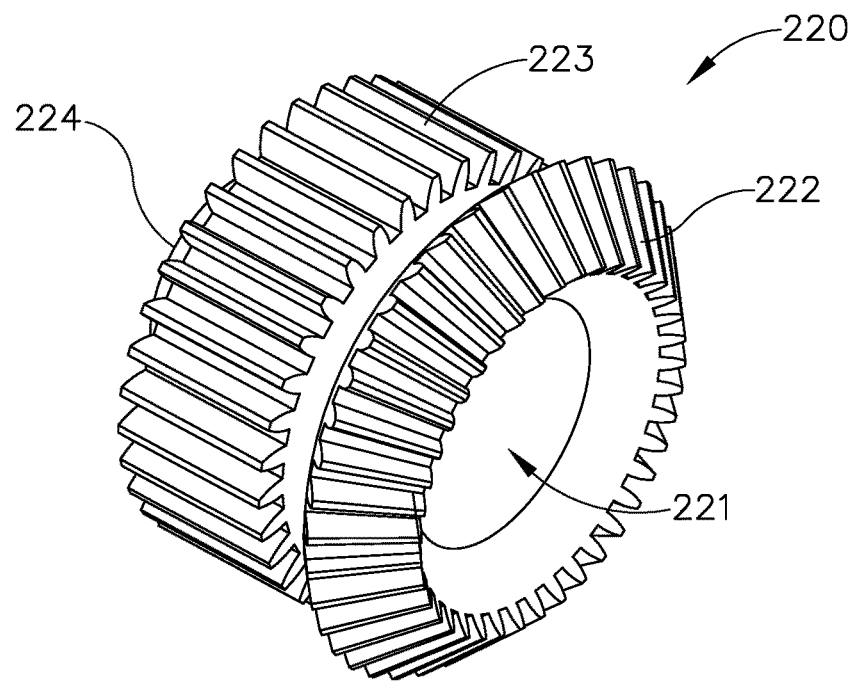
FIG. 12 depicts a perspective view of a first drive gear member of the shaft rotation drive components of FIG. 11.

As best seen in FIG. 12, idler member (220) includes a second bevel gear (222) and a first spur gear (223) unitarily fixed to each other by a coupling shaft (224). Therefore, rotation of second bevel gear (222) unitarily rotates first spur gear (223). Idler member (220) rotatably rests on a pair of legs (240, 245) extending above base plate (116). In some versions, idler member (220) is rotatably secured to legs (240, 245) by a bushing, bearings, and/or other features that facilitate rotation of idler member (220) relative to legs (240, 245). Legs (240, 245) extend from base plate (116) to a height allowing second bevel gear (222) to mesh with first bevel gear (212). Thus, rotation of first bevel gear (212) of first rotary member (210) provides rotation for second bevel gear (222) and first spur gear (223) of idler member (220).

It should be understood that rotation of first bevel gear (212) about a first axis defined by drive shaft (250) is converted into rotation of second bevel gear (222) about a second axis, which is orthogonal to the first axis and parallel with the longitudinal axis (LA) of shaft assembly (150). A clockwise (CW) rotation of second bevel gear (222) results in CW rotation of first spur gear (223). A counter-clockwise (CCW) rotation of second bevel gear (222) results in CCW rotation of first spur gear (223). Other suitable ways in which idler member (220) may be rotated will be apparent to those of ordinary skill in the art in view of the teachings herein.

Second rotary member (230) includes a second spur gear (232) and an elongated outer sheath (234), where both second spur gear (232) and elongated outer sheath (234) define a hollow portion (231). Second spur gear (232) is unitarily coupled to elongated outer sheath (234). Therefore, rotation of second spur gear (232) unitarily rotates elongated outer sheath (234). Legs (240, 245) also extend from base plate (116) to a height allowing first spur gear (223) to mesh with second spur gear (232). Thus, rotation of first spur gear (223) of idler member (220) provides rotation for second spur gear (232) of second rotary member (230). It should be understood that rotation of first spur gear (223) about second axis is converted into rotation of second spur gear (232) about longitudinal axis (LA) parallel with second axis. A CW rotation of first spur gear (223) results in CCW rotation of second spur gear (232). A CCW rotation of first spur gear (223) results in CW rotation of second spur gear (232). Other suitable ways in which second rotary member (230) may be rotated will be apparent to those of ordinary skill in the art in view of the teachings herein.

Figure 14A:
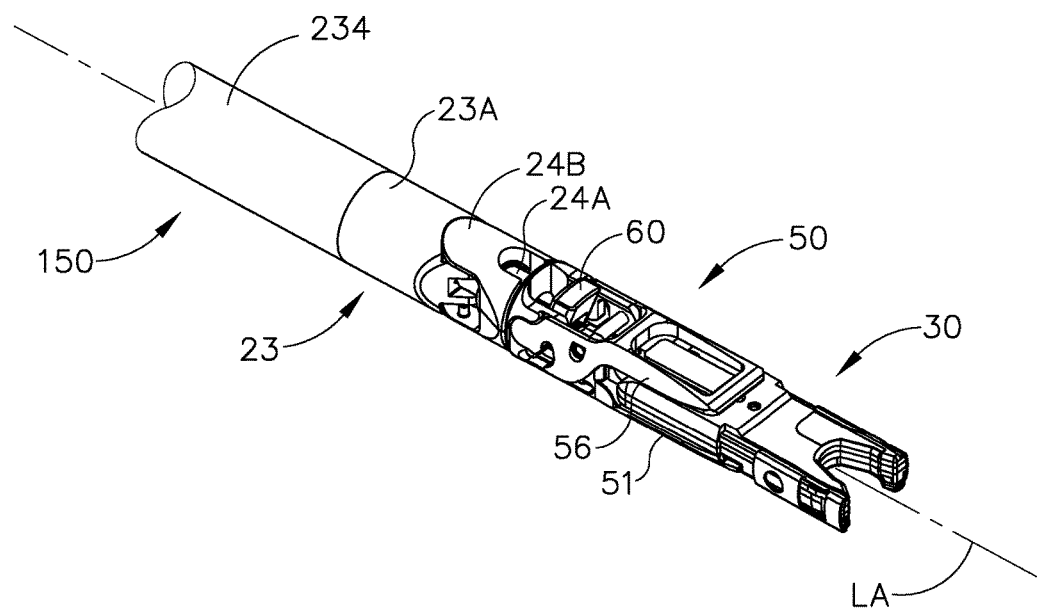
FIG. 14A depicts a perspective view of the cartridge receiving assembly of FIG. 2A, the cartridge of FIG. 3A, and a shaft assembly of the drive interface assembly of FIG. 7, all in a first angular position about the longitudinal axis of the shaft assembly.
Figure 14B:
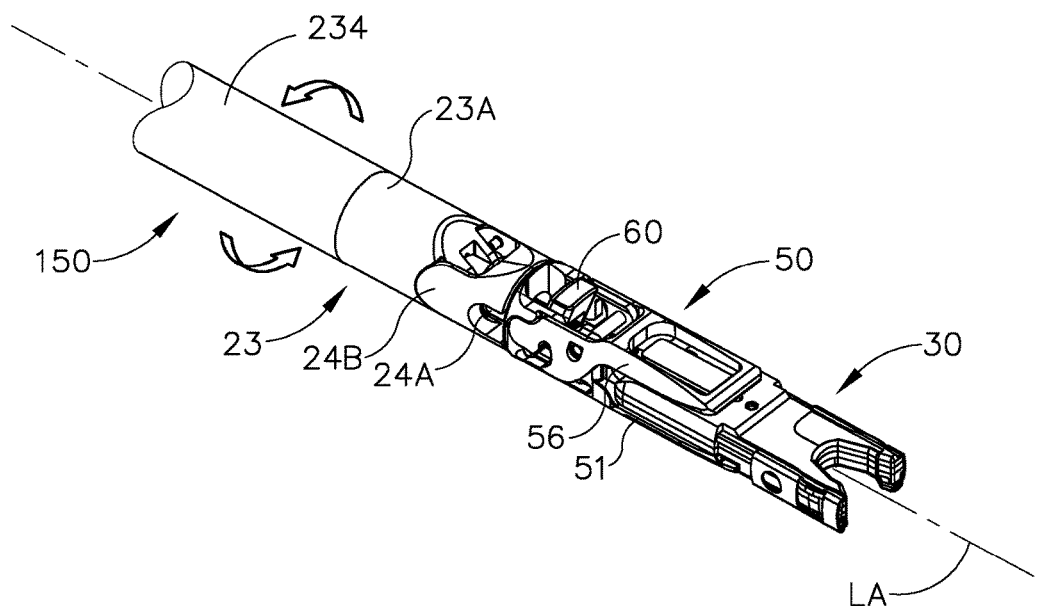
FIG. 14B depicts a perspective view of the cartridge receiving assembly of FIG. 2A, the cartridge of FIG. 3A, and the shaft assembly of the drive interface assembly of FIG. 7, with an outer sheath and an articulation joint of the shaft assembly driven to a second angular position about the longitudinal axis of the shaft assembly by the shaft rotation drive components of FIG. 11, while the cartridge receiving assembly of FIG. 2A and the cartridge of FIG. 3A remain in the first angular position.

Elongated outer sheath (234) extends along the longitudinal axis (LA) of shaft assembly (150). Elongated outer sheath (234) is substantially similar to elongated shaft (20) as mentioned above. Therefore, as can be seen in FIGS. 14A-14B, distal end of elongated outer sheath (234) is fixed to knuckle (23A) of articulation joint (23). As mentioned above, knuckle (23A) is coupled to bearing supports (24B, 24C). Bearing supports (24B, 24C) allow circumferential flange (24A) to rotate relative to bearing supports (24B, 24C). Also as mentioned above, circumferential flange (24A) is capable of rotating cartridge receiving assembly (50). Therefore, rotation of elongated outer sheath (234) does not rotate circumferential flange (24A) or cartridge receiving assembly (50). However, rotation of elongated outer sheath (234) will rotate articulation joint (23).

FIGS. 14A-14B show the ultimate result of rotating drive disc (120*a*) of sheath rotation drive (200). Rotation of drive disc (120*a*) rotates drive shaft (250) and first bevel gear (212). Rotation of first bevel gear (212) in turn rotates second bevel gear (222) and first spur gear (223) in the same direction and about the same axis. First spur gear (223) then rotates second spur gear (232) about a separate, parallel axis in the opposite angular direction. Elongated outer sheath (234) rotates about the same axis and same direction of second spur gear (232), thereby rotating articulation joint (23) about the longitudinal axis (LA) defined by shaft assembly (150). Such rotation may enable the operator to position articulation joint (23) at a preferred angular orientation, before or after articulation joint (23) is transitioned to an articulated state.

C. Exemplary Cartridge Receiving Assembly Rotation Drive Components

Figure 15:
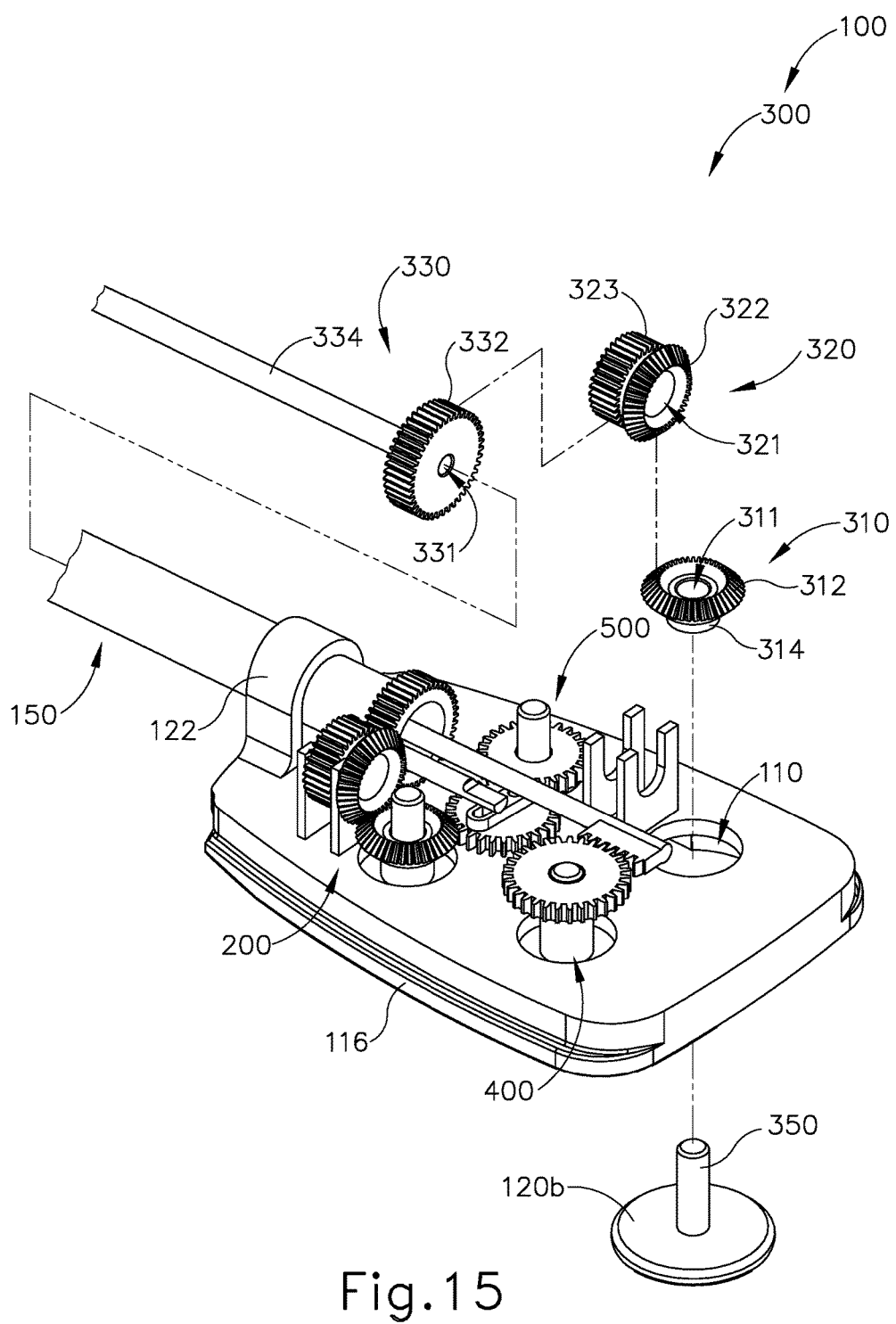
FIG. 15 depicts a perspective view of the drive interface assembly of FIG. 7, with cartridge receiving assembly rotation drive components shown exploded from the rest of the drive interface assembly.

As shown in FIG. 15, cartridge receiving assembly rotation drive (300) includes drive disc (120*b*), drive shaft (350), a first rotary member (310), an idler member (320), and a second rotary member (330). First rotary member (310) is configured substantially identical to first rotary member (210) as described above and as best shown in FIG. 13. In particular, first rotary member (310) comprises a first bevel gear (312) unitarily fixed to a coupling shaft (314). Coupling shaft (314) extends through aperture (110). First bevel gear (312) and coupling shaft (314) together define a bore (311). However, it should be noted that coupling shaft (314) alone may define bore (311). Bore (311) is dimensioned to receive drive shaft (350) through an interference fit so that first rotary member (310) and drive shaft (350) are unitarily fixed together. Of course, any other means of fixing drive shaft (250) to first rotary member (210) may be used, such as welding. It should be understood that rotation of drive disc (120*b*) also provides rotation to drive shaft (350) and first bevel gear (312).

Idler member (320) is configured substantially identical to idler member (220) as described above and as best shown in FIG. 12. In particular, idler member (320) includes a second bevel gear (322) and a first spur gear (323) unitarily fixed to each other by a coupling shaft (324). Therefore, rotation of second bevel gear (322) unitarily rotates first spur gear (323). Idler member (320) rotatably rests on a pair of legs (340, 345) extending above base plate (116). In some versions, idler member (320) is rotatably secured to legs (340, 345) by a bushing, bearings, and/or other features that facilitate rotation of idler member (320) relative to legs (340, 345). Legs (340, 345) extend from base plate (116) to a height allowing second bevel gear (322) to mesh with first bevel gear (312). Thus, rotation of first bevel gear (312) of first rotary member (310) provides rotation for second bevel gear (322) and first spur gear (323) of idler member (320).

It should be understood that rotation of first bevel gear (312) about a third axis defined by drive shaft (350) is converted into rotation of second bevel gear (322) about a fourth axis that is orthogonal with third axis and parallel with the longitudinal axis (LA) of shaft assembly. A CW rotation of second bevel gear (322) results is CW rotation of first spur gear (323). A counter-clockwise (CCW) rotation of second bevel gear (322) results in CCW rotation of first spur gear (323). Other suitable ways in which idler member (320) may be rotated will be apparent to those of ordinary skill in the art in view of the teachings herein.

Second rotary member (330) includes a second spur gear (332) and a rotational shaft (334), where both second spur gear (332) and rotational shaft (334) define a hollow portion (331). Rotational shaft (334) extends coaxially through elongated outer sheath (234) and rotates independently of elongated outer sheath (234). Rotational shaft (334) thus extends along the longitudinal axis (LA) of shaft assembly (150) and is rotatable about the longitudinal axis (LA) of shaft assembly (150). Second spur gear (332) is unitarily coupled to rotational shaft (334). Therefore, rotation of second spur gear (332) unitarily rotates rotational shaft (334). Legs (340, 345) also extend from base plate (116) to a height allowing first spur gear (323) to mesh with second spur gear (332). Thus, rotation of first spur gear (323) of idler member (320) provides rotation for second spur gear (332) of second rotary member (230). It should be understood that rotation of first spur gear (323) about fourth axis is converted into rotation of second spur gear (332) about longitudinal axis (LA) parallel with fourth axis. A CW rotation of first spur gear (323) results in CCW rotation of second spur gear (332). A CCW rotation of first spur gear (323) results in CW rotation of second spur gear (332). Other suitable ways in which second rotary member (330) may be rotated will be apparent to those of ordinary skill in the art in view of the teachings herein.

Figure 16:
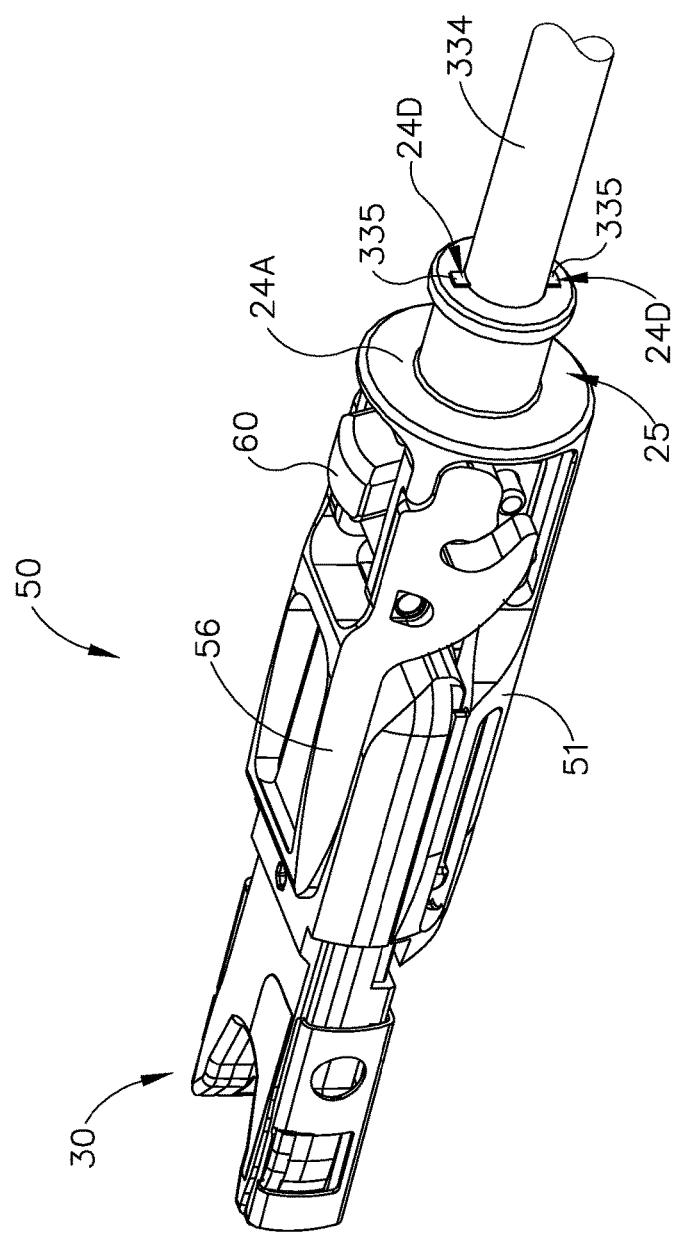
FIG. 16 depicts a perspective view of the distal end of a drive shaft of the cartridge receiving assembly rotation drive components of FIG. 15 coupled with the cartridge receiving assembly of FIG. 2A.

Rotational shaft (334) is substantially similar to drive rod (28) mentioned above in the fact that rotational shaft (334) is capable of rotating cartridge receiving assembly (50) about bearing (24) relative to elongated outer sheath (234). As depicted in FIG. 16, rotational shaft (334) includes a pair of outwardly extending keys (335) that are positioned within complementary keyways (24D) formed in a proximal coupling feature (25) of circumferential flange (24A). Of course, rotational shaft (334) may be rotatably secured to circumferential flange (24A) in any other suitable fashion as will be apparent to those skilled in the art in view of the teachings herein. It should also be understood that the distal portion of rotational shaft (334) may be flexible like distal bendable portion (28B) of drive rod (28). Such flexibility may prevent rotational shaft (334) from interfering with actuation of articulation joint (23). Rotational shaft (334) may still nevertheless transfer torsional drive forces to proximal flange (24A) despite being laterally flexible. By way of example only, the distal portion of rotational shaft (334) may be configured and operable in accordance with at least some of the teachings of U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein.

Figure 17A:
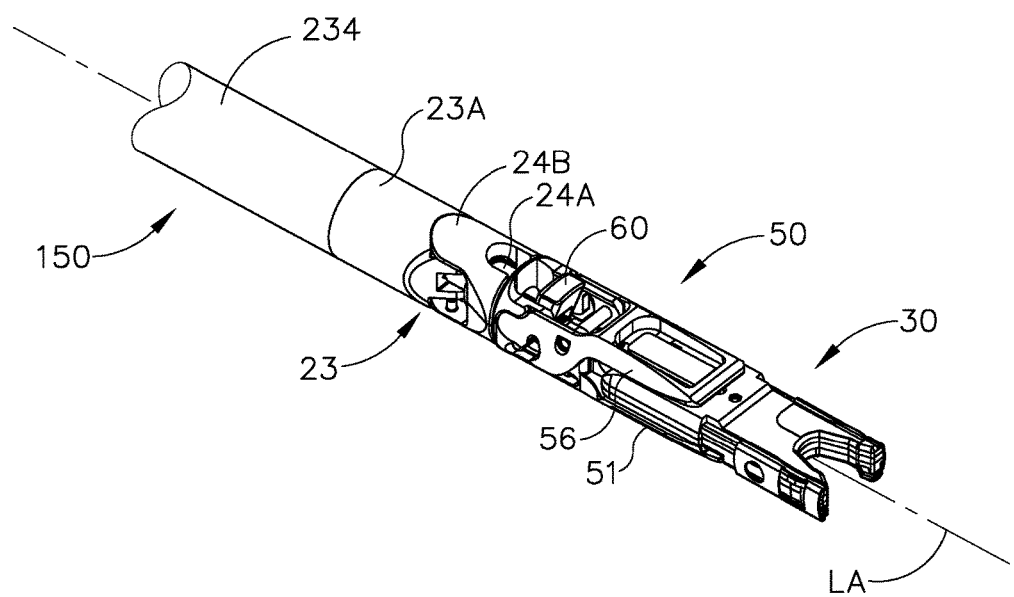
FIG. 17A depicts a perspective view of the cartridge receiving assembly of FIG. 2A, the cartridge of FIG. 3A, and the shaft assembly of the drive interface assembly of FIG. 7 all in a first angular position about the longitudinal axis of the shaft assembly.
Figure 17B:
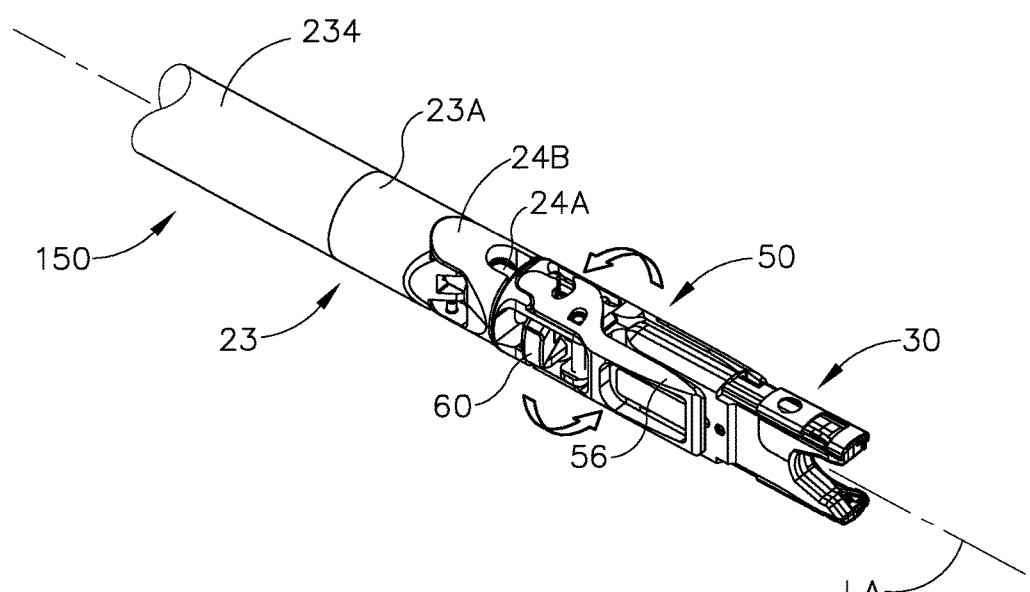
FIG. 17B depicts a perspective view of the cartridge receiving assembly of FIG. 2A and the cartridge of FIG. 3A both driven to a second angular position about the longitudinal axis of the shaft assembly by the cartridge receiving assembly rotation drive components of FIG. 15, while the shaft assembly remains in the first angular position.

As can be seen in FIGS. 17A-B, the distal end of elongated outer sheath (234) is fixed to knuckle (23A) of articulation joint (23). As mentioned above, knuckle (23A) is pivotably coupled to bearing supports (24B, 24C) to provide articulation of cartridge receiving assembly (50) and cartridge (30) relative to the longitudinal axis (LA) of shaft assembly (150). Bearing supports (24B, 24C) allow circumferential flange (24A) to rotate relative to bearing supports (24B, 24C), about the longitudinal axis (LA) of shaft assembly (150). Also as mentioned above, circumferential flange (24A) is capable of rotating cartridge receiving assembly (50). Therefore, rotation of rotational shaft (334) rotates circumferential flange (24A), cartridge receiving assembly (50), and cartridge (150) about longitudinal axis (LA) of shaft assembly (150), without rotating articulation joint (23) or elongated outer sheath (234). However, it should be noted that rotational shaft (334) is not similar to drive rod (28) in that rotational shaft (334) is not capable of actuating needle applier cartridge (30). That function is designated to needle drive (400) as described in greater detail below.

FIGS. 17A-B shows the ultimate result of rotating drive disc (120b) of cartridge receiving assembly rotation drive (300). Rotation of drive disc (120b) rotates drive shaft (350) and first bevel gear (312). Rotation of first bevel gear (312) in turn rotates second bevel gear (322) and first spur gear (323) in the same direction and about the same axis. First spur gear (323) then rotates second spur gear (332) about a separate, parallel axis in the opposite angular direction. Rotational shaft (334) rotates about the same axis and same direction of second spur gear (232), thereby rotating cartridge receiving assembly (50) and cartridge (30) about the longitudinal axis (LA) of shaft assembly (150).

D. Exemplary Needle Drive Components

Figure 18:
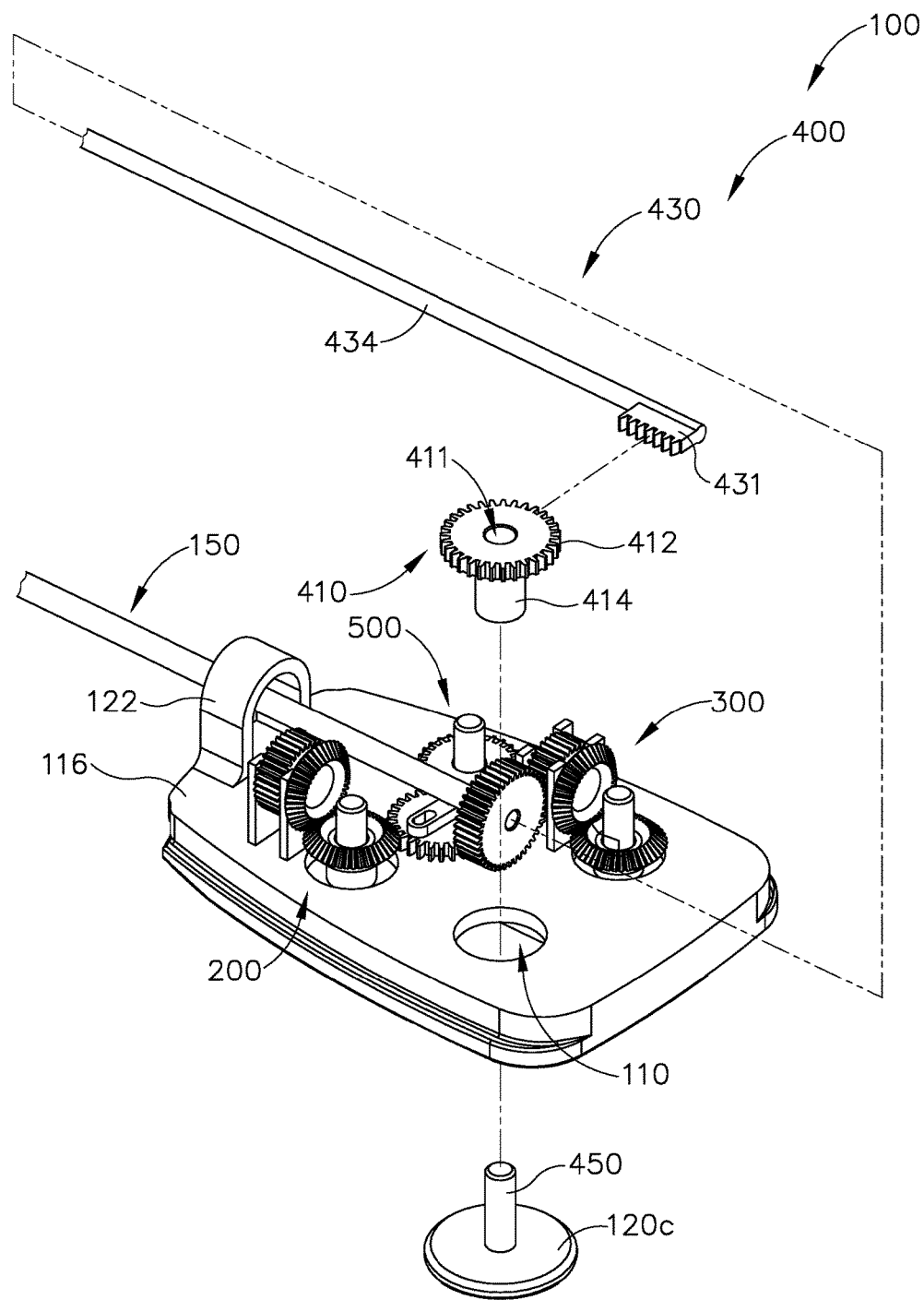
FIG. 18 depicts a perspective view of the drive interface assembly of FIG. 7, with needle drive components shown exploded from the rest of the drive interface assembly.

As shown in FIG. 18, needle drive (400) comprises a drive disc (120c), a drive shaft (450), a rotational member (410), and a translation member (430). Rotational member (410) includes a coupling shaft (414) unitarily fixed to a pinion (412). Coupling shaft (414) and pinion (412) together define a bore (411). However, it should be noted that coupling shaft (414) alone may define bore (411). Bore (411) is dimensioned to receive drive shaft (450) through an interference fit so that rotational member (410) and drive shaft (450) are unitarily fixed together. Of course, any other means of fixing drive shaft (250) to first rotary member (210) may be used, such as welding. It should be understood that rotation of drive disc (120c) also provides rotation to drive shaft (450) and pinion (412).

Translation member (430) includes a translating rod (434) and a rack (431). Translating rod (434) coaxially extends through both hollow portion (331) and circumferential flange (24A) along the longitudinal axis (LA) of shaft assembly (150). Translating rod (434) is slidably disposed within hollow portion (331) of rotational shaft (334). Distal end of translating rod (434) includes distal bendable portion (28B) coupled to mount (49). Therefore, translating rod (434) is capable of actuating needle applier cartridge (30) as shown in FIGS. 5A-5C, as done by drive rod (28) in the earlier example above. It should be noted that while drive rod (28) is capable of both actuating needle applier cartridge (30) and rotating cartridge receiving assembly (50), these functions are separately allocated among needle drive (400) and cartridge receiving assembly rotation drive (300) respectively, in the present example. Therefore, while distal bendable portion (28B) and proximal drive portion (28A) are fixed to each other on drive rod (28), they are separate from one another and are thus capable of independent movement from one another in drive assembly interface (100).

Rack (431) is fixed to translating rod (434). Therefore, linear movement of rack (431) creates linear movement of translating rod (434). Teeth of rack (431) mesh with teeth of pinion (412). Thus, rotation of pinion (412) provides linear movement of rack (431) along the longitudinal axis (LA) of shaft assembly (150). Rotation of drive disc (120c) rotates drive shaft (450) and pinion (412). It should be understood that rotation of pinion (412) occurs on a fifth axis defined by drive shaft (450), which is orthogonal with the longitudinal axis (LA) of shaft assembly (150). CW rotation of pinion (412) creates proximal translation of rack (431) and translating rod (434). CCW rotation of pinion (412) creates distal translation of rack (431) and translating rod (434). Therefore, as pinion (412) switches directions of rotation, translating rod (434) switches direction of translation along the longitudinal axis (LA) of shaft assembly (150), making needle driver (86) capable of a drive stroke and a return stroke as shown in FIGS. 5A-5C. Other suitable ways to create a drive stroke and a return stroke will be apparent to those of ordinary skill in the art in view of the teachings herein.

In some exemplary alternative versions, translating rod (434) and rotational shaft (334) are coupled together such that translating rod (434) will rotate with rotational shaft (334); yet such that translating rod (434) may rotate relative to rotational shaft (334). Thus, when rotational shaft (334) is driven to rotate as described above, such rotation may be communicated to cartridge receiving assembly (50) via translating rod (434); and translating rod (434) may still freely actuate needle applier cartridge (30) without interference from rotational shaft (334). By way of example only, translating rod (434) and rotational shaft (334) may be coupled together in a key-keyway relationship.

As another merely illustrative example, the distal portion of shaft assembly (150) may include a sliding key coupled cable connector, which could be located within outer sheath (234) at a location that is distal to drive assembly interface (100). Such a connector may enable translating rod (434) and rotational shaft (334) to each independently induce motion on a single distal drive cable. For instance, if rotational shaft (334) is actuated and translating rod (434) is held stationary, this will rotate the distal drive cable and thereby rotate cartridge receiving assembly (50). If translating rod (434) is actuated and rotational shaft (334) is held stationary, this will actuate needle applier cartridge (30). Other suitable configurations and relationships will be apparent to those of ordinary skill in the art in view of the teachings herein.

E. Exemplary Articulation Drive Components

Figure 19:
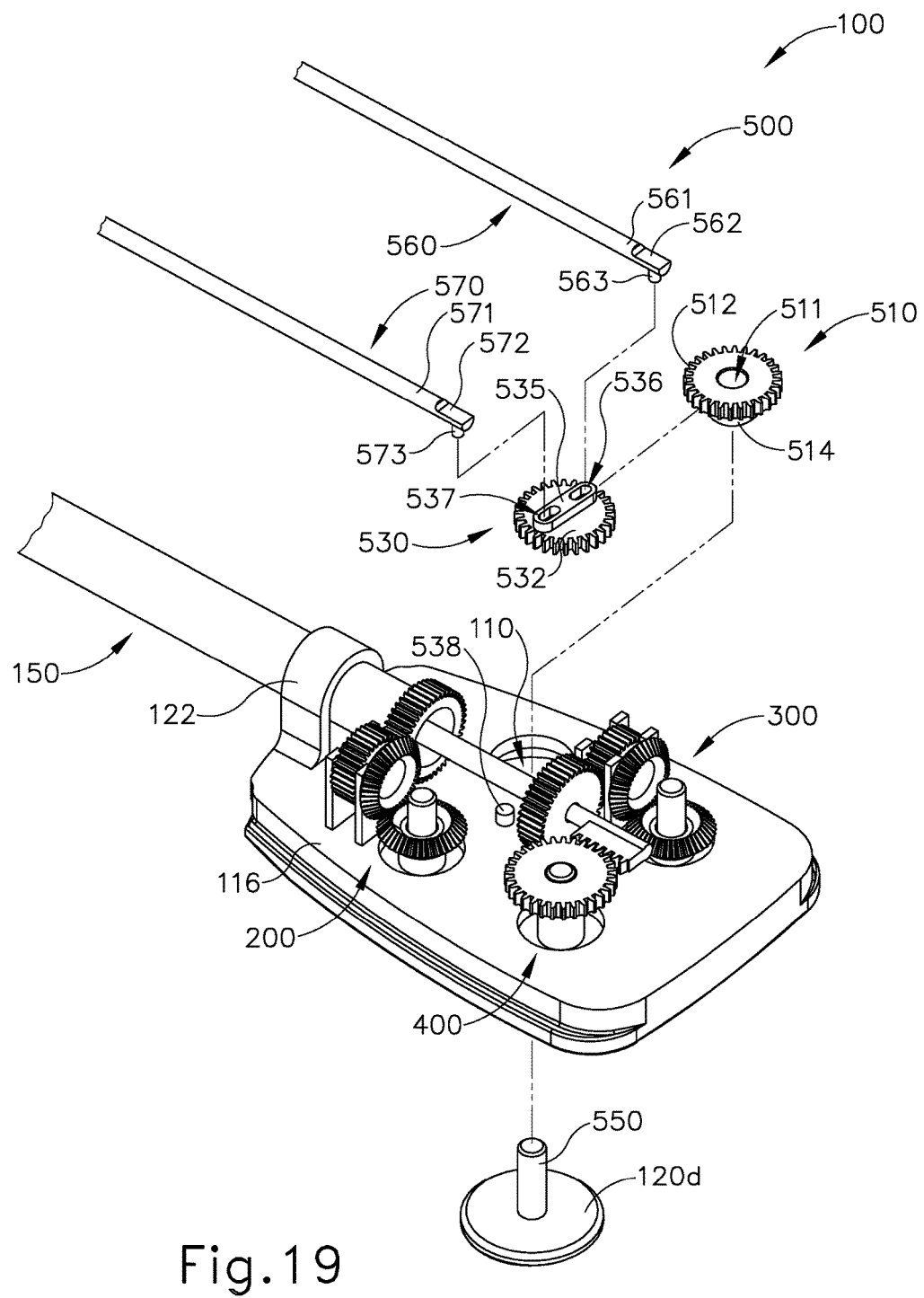
FIG. 19 depicts a perspective view of the drive interface assembly of FIG. 7, with articulation drive components shown exploded from the rest of the drive interface assembly.
Figure 20:
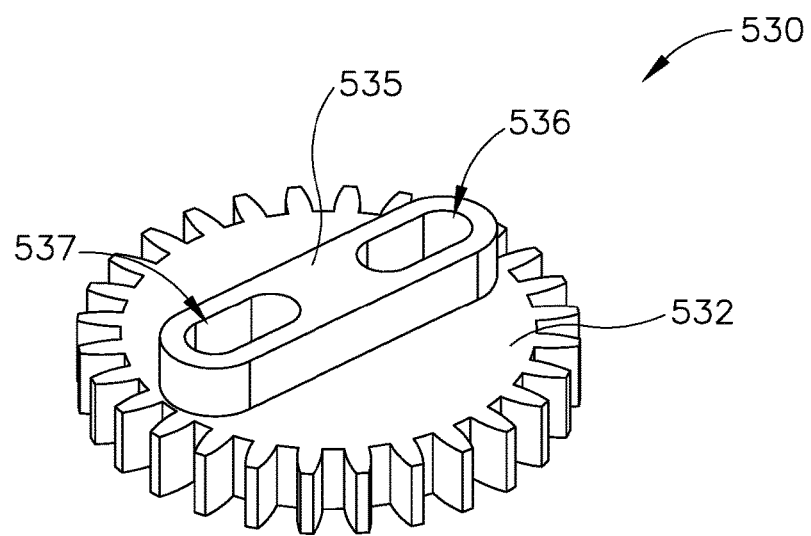
FIG. 20 depicts a perspective view of a gear member of the articulation drive components of FIG. 19.
Figure 21:
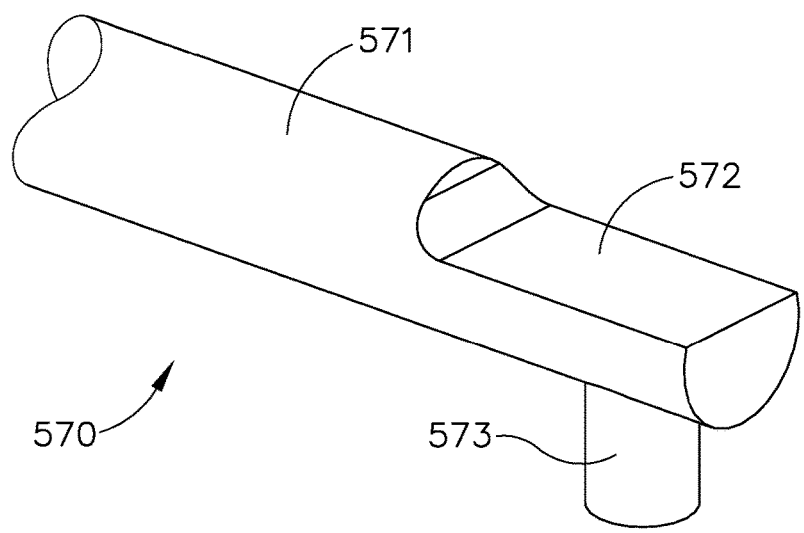
FIG. 21 depicts a perspective view of a proximal end of an articulation drive rod of the articulation drive components of FIG. 19.

As shown in FIG. 19, articulation drive (500) includes a drive disc (120d), a drive shaft (550), a rotational member (510), an articulation base (530), and articulation rods (560, 570). Rotational member (510) includes a coupling shaft (514) unitarily fixed to first spur gear (512). Coupling shaft (514) extends through aperture (110). Coupling shaft (514) and first spur gear (512) together define a bore (511). However, it should be noted that coupling shaft (514) alone may define bore (511). Bore (511) is dimensioned to receive drive shaft (450) through an interference fit so that rotational member (510) and drive shaft (550) are unitarily fixed together. Of course, any other means of fixing drive shaft (550) to rotational member (510) may be used, such as welding. It should be understood that rotation of drive disc (120d) also provides rotation to drive shaft (510) and first spur gear (512).

Articulation base (530) includes a second spur gear (532), a cam feature (535), and a post (538) extending from the face of base plate (116). Second spur gear (532) is rotatable supported on post (538). First spur gear (512) meshes with second spur gear (532) so that rotation of first spur gear (512) rotates second spur gear (532) and cam feature (535) about post (538). Rotation of drive disc (120d) thus also provides rotation of second spur gear (532) and cam feature (535). It should be understood that rotation of first spur gear (512) about a sixth axis defined by drive shaft (550) is converted in rotation of second spur gear (532) about a seventh axis defined by post (538) that is parallel with the sixth axis. A CW rotation of first spur gear (512) results in a CCW rotation of second spur gear (532). A CCW rotation of first spur gear (512) results in a CCW rotation of second spur gear (532). Other suitable ways in which second spur gear (532) may be rotated will be apparent to those of ordinary skill in the art in view of the teachings herein.

Post (538) receives the center of second spur gear (532) so that second spur gear (532) may rotate about the seventh axis. Cam feature (535) is unitarily fixed to second spur gear (532) such that cam feature (535) rotates with second spur gear (532) about the seventh axis defined by post (538). Cam feature (535) includes two slots (536, 537) laterally spaced from the seventh axis. Articulation rods (560, 570) include longitudinal members (561, 571) and transverse members (563, 573) respectively. Transverse members (563, 573) are inserted into respective slots (536, 537), such that transverse members (563, 573) are configured and positioned to serve as cam followers.

Longitudinal members (561, 571) extend through elongated outer sheath (234) and terminate in distal ends similar to the distal ends of rods (27A, 27B) mentioned above. Therefore, longitudinal members (561, 571) extend through elongated outer sheath (234), through knuckle (23A), and connect to pins (29A, 29B) on bearing support (24C). As shown in FIG. 7, longitudinal members (561, 571) extend longitudinally through outer sheath (234) along respective longitudinal axes that are parallel to yet offset from the longitudinal axis (LA) of shaft assembly (150).

As shown in FIGS. 22A-22C, rotation of cam feature (535) will opposingly push and pull actuations rods (560, 570) due to slots (536, 537) being laterally spaced from the seventh axis defined by post (538). In other words, cam feature (535) is operable to drive actuation rods (560, 570) at the same time in opposite longitudinal directions, such that actuation rod (560) will translate distally while actuation rod (570) translates proximally; and such that actuation rod (570) will translate distally while actuation rod (560) translates proximally. Because pins (29A, 29B) are laterally spaced from the pivoting axis, the simultaneous push and pull action will in turn articulate cartridge receiving assembly (50) about joint (23) relative to elongated outer sheath (234) as shown in FIGS. 23A-23C. In particular, rotating spur gear (532) CCW from the position shown in FIG. 22A to the position shown in FIG. 22B will result in cartridge receiving assembly (50) and cartridge assembly (30) being deflected laterally away to the left of the longitudinal axis (LA) of shaft assembly (150) at articulation joint (23), as shown in the transition from FIG. 23A to FIG. 23B. Similarly, rotating spur gear (532) CW from the position shown in FIG. 22A to the position shown in FIG. 22C will result in cartridge receiving assembly (50) and cartridge assembly (30) being deflected laterally away to the right of the longitudinal axis (LA) of shaft assembly (150) at articulation joint (23), as shown in the transition from FIG. 23A to FIG. 23C.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a cartridge receiving assembly, wherein the cartridge receiving assembly is operable to receive a needle driving cartridge; (b) a shaft assembly, wherein the shaft assembly defines a longitudinal axis, wherein the shaft assembly comprises: (i) a distal end, wherein the cartridge receiving assembly is positioned at the distal end of the shaft assembly, (ii) a proximal end, and (iii) a first actuation member, wherein the first actuation member is operable to actuate the cartridge receiving assembly to thereby drive a needle from a needle driving cartridge received in the cartridge receiving assembly; and (c) an interface assembly positioned at the proximal end of the shaft assembly, the interface assembly comprising: (i) a base, and (ii) a plurality of drive shafts extending upwardly from the base, wherein the drive shafts extend along respective axes that are perpendicular to the longitudinal axis of the shaft assembly, wherein the drive shafts are rotatable independently relative to each other, wherein a first drive shaft of the plurality of drive shafts is operable to drive the first actuation member.

Example 2

The surgical instrument of Example 1, wherein the first actuation member comprises a longitudinally extending shaft, wherein the longitudinally extending shaft is operable to translate longitudinally along the longitudinal axis of the shaft assembly to thereby actuate the cartridge receiving assembly.

Example 3

The surgical instrument of Example 2, wherein the first actuation member further comprises a rack secured to the longitudinally extending shaft, wherein the first drive shaft is operable to rotate a pinion, wherein the pinion is coupled with the rack such that the longitudinally extending shaft is configured to translate longitudinally along the longitudinal axis of the shaft assembly in response to rotation of the first drive shaft.

Example 4

The surgical instrument of any one or more of Examples 1 through 3, wherein the shaft assembly further comprises an articulation joint, wherein the articulation joint is operable to deflect the cartridge receiving assembly laterally away from the longitudinal axis of the shaft assembly.

Example 5

The surgical instrument of Example 4, wherein the shaft assembly further comprises at least one articulation drive member, wherein the at least one articulation drive member is configured to translate longitudinally to actuate the articulation joint to thereby deflect the cartridge receiving assembly laterally away from the longitudinal axis of the shaft assembly.

Example 6

The surgical instrument of Example 5, wherein the plurality of drive shafts further comprises a second drive shaft coupled with the at least one articulation drive member, wherein the second drive shaft is operable cause the at least one articulation drive member to translate longitudinally in response to rotation of the second drive shaft.

Example 7

The surgical instrument of Example 6, wherein the interface assembly further comprises a pair of spur gears coupling between the second drive shaft with the articulation drive member.

Example 8

The surgical instrument of Example 7, wherein a first spur gear of the pair of spur gears comprises a cam feature, wherein the articulation drive member comprises a cam follower engaged with the cam feature of the first spur gear.

Example 9

The surgical instrument of any one or more of Examples 6 through 7, wherein the at least one articulation member comprises a first articulation drive member and a second articulation drive member, wherein the first and second articulation drive members are operable to translate longitudinally in opposing directions simultaneously to thereby deflect the cartridge receiving assembly laterally away from the longitudinal axis of the shaft assembly.

Example 10

The surgical instrument of Example 9, wherein the second drive shaft is operable cause the first and second articulation drive members to translate longitudinally in opposing directions simultaneously in response to rotation of the second drive shaft.

Example 11

The surgical instrument of any one or more of Examples 1 through 10, wherein the shaft assembly further comprises: (i) an outer sheath, and (ii) a second actuation member, wherein the second actuation member is operable to rotate the cartridge receiving assembly independently of the outer sheath about the longitudinal axis of the shaft assembly.

Example 12

The surgical instrument of Example 11, wherein the wherein the plurality of drive shafts further comprise a second drive shaft operable to drive the second actuation member.

Example 13

The surgical instrument of any one or more of Examples 1 through 12, wherein the shaft assembly further comprises: (i) an outer sheath, and (ii) an articulation joint, wherein the articulation joint is operable to deflect the cartridge receiving assembly laterally away from the longitudinal axis of the shaft assembly.

Example 14

The surgical instrument of Example 13, wherein the outer sheath is rotatable about the longitudinal axis of the shaft assembly, wherein the articulation joint is configured to rotate with the outer sheath about the longitudinal axis of the shaft assembly independently of the cartridge receiving assembly.

Example 15

The surgical instrument of Example 14, wherein the wherein the plurality of drive shafts further comprise a second drive shaft operable to rotate the outer sheath and the articulation joint together about the longitudinal axis of the shaft assembly.

Example 16

The surgical instrument of any one or more of Examples 1 through 15, further comprising a needle driving cartridge received in the cartridge receiving assembly.

Example 17

The surgical instrument of Example 16, wherein the needle driving cartridge comprises: (i) a curved needle, (ii) a length of suture secured to the curved needle, and (iii) a needle drive assembly operable to drive the curved needle along an orbital path, wherein the first actuation member is operable to actuate the needle drive assembly.

Example 18

The surgical instrument of Example 17, wherein the needle drive assembly of the needle driving cartridge is operable to drive the curved needle along an orbital path that encircles an axis that is non-parallel with the longitudinal axis of the shaft assembly.

Example 19

A surgical instrument comprising: (a) a curved needle; (b) a length of suture secured to the curved needle; (c) a needle drive assembly operable to drive the curved needle along an orbital path; (d) a shaft assembly, wherein the shaft assembly defines a longitudinal axis, wherein the shaft assembly comprises: (i) a distal end, wherein the needle drive assembly is positioned at the distal end of the shaft assembly, (ii) a proximal end, and (iii) an actuation member, wherein the actuation member is operable to actuate the needle drive assembly to thereby drive the needle along the orbital path; and (e) an interface assembly positioned at the proximal end of the shaft assembly, the interface assembly comprising: (i) a base, and (ii) a plurality of drive shafts extending upwardly from the base, wherein the drive shafts extend along respective axes that are perpendicular to the longitudinal axis of the shaft assembly, wherein the drive shafts are rotatable independently relative to each other, wherein a first drive shaft of the plurality of drive shafts is operable to drive the actuation member.

Example 20

A surgical instrument comprising: (a) a cartridge receiving assembly, comprising: (i) a first jaw, and (ii) a second jaw pivotable relative to the first jaw from an open position to a closed position, wherein the closed position is configured to hold a needle driving cartridge between the first jaw and the second jaw; (b) a shaft assembly, wherein the shaft assembly defines a longitudinal axis, wherein the shaft assembly comprises: (i) a distal end, wherein the cartridge receiving assembly is positioned at the distal end of the shaft assembly, (ii) a proximal end, and (iii) a first actuation member, wherein the first actuation member is operable to actuate the cartridge receiving assembly to thereby drive a needle from a needle driving cartridge received in the cartridge receiving assembly; and (c) an interface assembly positioned at the proximal end of the shaft assembly, the interface assembly comprising: (i) a base, and (ii) a plurality of drive shafts extending upwardly from the base, wherein the drive shafts extend along respective axes that are perpendicular to the longitudinal axis of the shaft assembly, wherein the drive shafts are rotatable independently relative to each other, wherein a first drive shaft of the plurality of drive shafts is operable to drive the first actuation member.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a cartridge receiving assembly, wherein the cartridge receiving assembly is operable to receive a needle driving cartridge;
   (b) a shaft assembly, wherein the shaft assembly defines a longitudinal axis, wherein the shaft assembly comprises:
      (i) a distal end, wherein the cartridge receiving assembly is positioned at the distal end of the shaft assembly,
      (ii) a proximal end, and
      (iii) a first actuation member, wherein the first actuation member is operable to actuate the cartridge receiving assembly to thereby drive a needle from a needle driving cartridge received in the cartridge receiving assembly and wherein the shaft assembly further comprises: (i) an outer sheath, and (ii) a second actuation member, wherein the second actuation member is operable to rotate the cartridge assembly independently of the outer sheath about the longitudinal axis of the shaft assembly; and
   (c) an interface assembly positioned at the proximal end of the shaft assembly, the interface assembly comprising:
      (i) a base, and
      (ii) a plurality of drive shafts extending upwardly from the base, wherein the drive shafts extend along respective axes that are perpendicular to the longitudinal axis of the shaft assembly, wherein the drive shafts are rotatable independently relative to each other, wherein a first drive shaft of the plurality of drive shafts is operable to drive the first actuation member, wherein the plurality of drive shafts further comprises a second drive shaft operable to drive the second actuation member.

2. The surgical instrument of claim 1, wherein the first actuation member comprises a longitudinally extending shaft, wherein the longitudinally extending shaft is operable to translate longitudinally along the longitudinal axis of the shaft assembly to thereby actuate the cartridge receiving assembly.

3. The surgical instrument of claim 2, wherein the first actuation member further comprises a rack secured to the longitudinally extending shaft, wherein the first drive shaft is operable to rotate a pinion, wherein the pinion is coupled with the rack such that the longitudinally extending shaft is configured to translate longitudinally along the longitudinal axis of the shaft assembly in response to rotation of the first drive shaft.

4. The surgical instrument of claim 1, wherein the shaft assembly further comprises an articulation joint, wherein the articulation joint is operable to deflect the cartridge receiving assembly laterally away from the longitudinal axis of the shaft assembly.

5. The surgical instrument of claim 4, wherein the shaft assembly further comprises at least one articulation drive member, wherein the at least one articulation drive member is configured to translate longitudinally to actuate the articulation joint to thereby deflect the cartridge receiving assembly laterally away from the longitudinal axis of the shaft assembly.

6. The surgical instrument of claim 5, wherein the plurality of drive shafts further comprises the second drive shaft coupled with the at least one articulation drive member, wherein the second drive shaft is operable to cause the at least one articulation drive member to translate longitudinally in response to rotation of the second drive shaft.

7. The surgical instrument of claim 6, wherein the interface assembly further comprises a pair of spur gears coupling between the second drive shaft with the articulation drive member.

8. The surgical instrument of claim 7, wherein a first spur gear of the pair of spur gears comprises a cam feature, wherein the articulation drive member comprises a cam follower engaged with the cam feature of the first spur gear.

9. The surgical instrument of claim 6, wherein the at least one articulation member comprises a first articulation drive member and a second articulation drive member, wherein the first and second articulation drive members are operable to translate longitudinally in opposing directions simultaneously to thereby deflect the cartridge receiving assembly laterally away from the longitudinal axis of the shaft assembly.

10. The surgical instrument of claim 9, wherein the second drive shaft is operable to cause the first and second articulation drive members to translate longitudinally in opposing directions simultaneously in response to rotation of the second drive shaft.

11. The surgical instrument of claim 1, wherein the shaft assembly further comprises:
(i) the outer sheath, and
(ii) an articulation joint, wherein the articulation joint is operable to deflect the cartridge receiving assembly laterally away from the longitudinal axis of the shaft assembly.

12. The surgical instrument of claim 11, wherein the outer sheath is rotatable about the longitudinal axis of the shaft assembly, wherein the articulation joint is configured to rotate with the outer sheath about the longitudinal axis of the shaft assembly independently of the cartridge receiving assembly.

13. The surgical instrument of claim 12, wherein the plurality of drive shafts further comprise the second drive shaft operable to rotate the outer sheath and the articulation joint together about the longitudinal axis of the shaft assembly.

14. The surgical instrument of claim 1, further comprising a needle driving cartridge received in the cartridge receiving assembly.

15. The surgical instrument of claim 14, wherein the needle driving cartridge comprises:
(i) a curved needle,
(ii) a length of suture secured to the curved needle, and
(iii) a needle drive assembly operable to drive the curved needle along an orbital path, wherein the first actuation member is operable to actuate the needle drive assembly.

16. The surgical instrument of claim 15, wherein the needle drive assembly of the needle driving cartridge is operable to drive the curved needle along an orbital path that encircles an axis that is non-parallel with the longitudinal axis of the shaft assembly.

17. A surgical instrument comprising:
(a) a cartridge receiving assembly, comprising:
(i) a first jaw, and
(ii) a second jaw pivotable relative to the first jaw from an open position to a closed position, wherein the closed position is configured to hold a needle driving cartridge between the first jaw and the second jaw;
(b) a shaft assembly, wherein the shaft assembly defines a longitudinal axis, wherein the shaft assembly comprises:
(i) a distal end, wherein the cartridge receiving assembly is positioned at the distal end of the shaft assembly,
(ii) a proximal end, and
(iii) a first actuation member, wherein the first actuation member is operable to actuate the cartridge receiving assembly to thereby drive a needle from a needle driving cartridge received in the cartridge receiving assembly; and
(c) an interface assembly positioned at the proximal end of the shaft assembly, the interface assembly comprising:
(i) a base, and
(ii) a plurality of drive shafts extending upwardly from the base, wherein the drive shafts extend along respective axes that are perpendicular to the longitudinal axis of the shaft assembly, wherein the drive shafts are rotatable independently relative to each other, wherein a first drive shaft of the plurality of drive shafts is operable to drive the first actuation member.

* * * * *